(12) United States Patent
Shoichet et al.

(10) Patent No.: US 9,498,539 B2
(45) Date of Patent: Nov. 22, 2016

(54) AFFINITY-BASED CONTROLLED RELEASE SYSTEM

(71) Applicants: Molly Sandra Shoichet, Toronto, CA (US); Katarina Vulic, Oakville, CA (US)

(72) Inventors: Molly Sandra Shoichet, Toronto, CA (US); Katarina Vulic, Oakville, CA (US)

( * ) Notice: Subject to any disclaimer, the term of this patent is extended or adjusted under 35 U.S.C. 154(b) by 34 days.

(21) Appl. No.: 13/728,946

(22) Filed: Dec. 27, 2012

(65) Prior Publication Data

US 2014/0187487 A1  Jul. 3, 2014

(51) Int. Cl.
   A61K 47/48    (2006.01)
   B82Y 5/00     (2011.01)

(52) U.S. Cl.
   CPC ... *A61K 47/48361* (2013.01); *A61K 47/48784* (2013.01); *B82Y 5/00* (2013.01)

(58) Field of Classification Search
   None
   See application file for complete search history.

(56) References Cited

FOREIGN PATENT DOCUMENTS

WO    2006076344    7/2006
WO    2007072461    6/2007

OTHER PUBLICATIONS

Lee et al.,PNAS, 2019,107, 8, 3340-3345.*
Stollar et al., J. of Bio. Chem, 2009, 284, 39, 26918-26927.*
Lee et al., PNAS, 2010, 107, 8, 3340-3345.*
Baumann et al., J. of Controlled Releasee, 2009, 138, 205-213.*
Stollar et al., J. of Bio. Chem., 2009, 284, 39, 26918-26927.*
Lee et al., PNAS, 2010, 107(8), 3340-3345.*
Baumann et al., J. of Controlled Release, 2009, 138, 205-213.*
Stollar et al., J. of Bio. Chem., 2009, 284(39), 26918-26927.*
Bradbury, E. J. et al. Chondroitinase ABC promotes functional recovery after spinal cord injury. S. B. Nature 2002. 416. 636-640.
Schnell, L. et al. Neurotrophin-3 enhances sprouting of corticospinal tract during development and after adult spinal cord lesion. Nature 1994,. 367. 170-173.
Moon, L. D. F. et al. Regeneration of CNS axons back to their target following treatment of adult rat brain with chondroitinase ABC. Nature Neuroscience. 2001. 4. 465-466.
Putney, S. D.; Burke, P. A. Improving protein therapeutics with sustained-release formulations. Nat Biotech 1998. 16. 153-157.
LaVan, D. A. et al. Small-scale systems for in vivo drug delivery. Nat Biotech 2003. 21. 1184-1191.
Wang, N. X et al. Affinity-Based Drug Delivery. Macromolecular Bioscience 2011. 11. 321-332.
Perez, C. et al. Recent trends in stabilizing protein structure upon encapsulation and release from bioerodible polymers. Journal of Pharmacy and Pharmacology 2002. 54. 301-313.
Kumar, V. et al. Thermodynamic Limits on Drug Loading in Nanoparticle Cores. Journal of Pharmaceutical Sciences 2008. 97. 4904-4914.
Ho, Y.-C. et al. Heparin-functionalized chitosan-alginate scaffolds for controlled release of growth factor. International Journal of Pharmaceutics 2009. 376. 69-75.
Lee, J. S et al. Heparin conjugated polymeric micelle for long-term delivery of basic fibroblast growth factor. Journal of Controlled Release 2007. 117. 204-209.
Tae, G. et al. PEG-cross-linked herparin is an affinity hydrogel for sustained release of vascular endothelial growth factor Journal of Biomaterials Science—Polymer Edition 2006. 17. 187-197.
Yoon, J. J. et al. Heparin-immobilized biodegradable scaffolds for local and sustained release of angiogenic growth factor. Journal of Biomedical Materials Research Part A 2006. 79A. 934-942.
Maxwell, D. J. et al. Development of rationally designed affinity-based drug delivery systems. Acta Biomaterialia 2005. 1. 101-113.
Sakiyama-Elbert, S. E. et al. Controlled release of nerve growth factor from a heparin-containing fibrin-based cell ingrowth matrix. Journal of Controlled Release 2000. 69. 149-158.
Sakiyama-Elbert, S. E. et al. Development of fibrin derivatives for controlled release of heparin-binding growth factors. Journal of Controlled Release 2000. 65. 389-402.
Wood, M. D. et al. Controlled release of glial-derived neurotrophic factor from fibrin matrices containing an affinity-based delivery system. Journal of Biomedical Materials Research Part A 2009. 89A 909-918.
Wood, M. D. et al. Release rate controls biological activity of nerve growth factor released from fibrin matrices containing affinity-based delivery systems. Journal of Biomedical Materials Research Part A 2008. 84A. 300-312.
Nie, T.; Baldwin et al. Production of heparin-functionalized hydrogels for the development of responsive and controlled growth factor delivery systems. Journal of Controlled Release 2007. 122. 287-296.
Lin, C.-C. et al. Controlling Affinity Binding with Peptide-Functionlized Poly (ethlene glycol) Hydrogels. Advanced Functional Materials. 2009. 19. 2325-2331.
Fan, J. A. et al. Linear Ordered Collagen Scaffolds Loaded with Collagen-Binding Neurotrophin-3 Promote Axonal Regeneration and Partial Functional Recovery after Complete Spinal Cord Transection. Journal of Neurotrauma 2010. 27. 1671-1683.
Gupta, D. et al. Fast-gelling injectable blend of hyaluronan and methylcellulose for intrathecal, localized delivery to the injured spinal cord. Biomaterials 2006. 27. 2370-2379.
Cooke, M. J. et al. Controlled epi-cortical delivery of epidermal growth factor for the stimulation of endogenous neural stem stem cell proliferation in stroke-injured brain. Biomaterials 2011. 32. 5688-5697.
Baumann, M. D. et al. An injectable drug delivery platform for sustained combination therapy. Journal of Controlled Release 2009. 138. 205-213.
Kang, C. E. et al. Poly(ethylen glycol) modification enhances penetration of fibroblast growth factor 2 to injured cord tissue from an intrathecal delivery system. Journal of Controlled Release 2010. 144. 25-31.

(Continued)

*Primary Examiner* — James H Alstrum Acevedo
*Assistant Examiner* — Roy Teller
(74) *Attorney, Agent, or Firm* — Hill & Schumacher

(57) ABSTRACT

Prolonged or extended release of bioactive protein is achieved using an affinity-based approach which exploits the specific binding of Src homology 3 (SH3) domain with short proline-rich peptides. Specifically, methylcellulose was modified with SH3-binding peptides (MC-peptide) with either a weak affinity or strong affinity for SH3. Controlled release of chondroitinase ABC (ChABC) is also described.

20 Claims, 15 Drawing Sheets

(56) References Cited

OTHER PUBLICATIONS

Thuret, S. et al. Therapeutic interventions after spinal cord injury. Nat Rev Neurosci 2006. 7. 628-643.
Ramer, M. S. et al. Functional regeneration of sensory axons into the adult spinal cord. Nature 2000. 403. 312-316.
Rabchevsky, A. G. et al. Basic Fibroblast Growth Factor (bFGF) Enhances Functional Recovery Following severe Spinal Cord Injury to the Rat. Experimental Neurology 2000. 164. 280-291.
Brunswick, M. et al. Picogram Quantities of Anti-Ig Antibodies Coupled to Dextran Induce B Cell Proliferation.The Journal of Immunology 1988. 140. 3364-3372.
Shu, X. Z. et al. Disulfide Cross-Linked Hyaluronan Hydrogels. Biomacromolecules 2002. 3. 1304-1311.
Stollar, E. J. et al. Structural, Functional, and Bioinformatic Studies Demonstrate the Crucial Role of an Extended Peptide Binding Site for the SH3 Domain of Yeast Abp 1p. Journal of Biological Chemistry 2009. 284. 26918-26927.
Deyev, S. M. et al. Design of Multivalent complexes using the barnase-barstar module. Nat Biotech 2003. 21. 1486-1492.
Wylie, R. G. et al. Three-Dimensional Spatial Patterning of Proteins in Hydrogels. Biomacromolecules 2011. 12. 3789-3796.
Ritger, P. L. et al. A simple equation for description of solute release I Fickian and Non-Fickian Release from Non-Swellable Devices in the form of slabs, spheres, cylinders of discs. Journal of Controlled Release 198T 5. 23-36.
Huang, X. et al. On the importance and mechanisms of burst release in matrix-controlled drug delivery systems. Journal of Controlled Release 2001 73. 121-136.
Kang, C. E. et al. A New Paradigm for Local and Sustained Release of Therapeutic Molecules to the Injured Spinal Cord for Neuroprotection and Tissue Repair. Tissue Engineering Part A 15. 595-604. (2009).
Suzuki, T. et al., Chonodritinase ABC Treatment Enhances Synaptogenesis Between Transplant and Host Neurons in Model of Retinal Degeneration. Cell Transplantation 16. 493-503 (2007).
Ma, J. et al. Combining chondroitinase ABC and growth factors promotes the integration of murine retinal progenitor cells transplanted into Rho mice. Molecular Vision 17. 1759-1770 (2011).
Soleman, S. et al. Delayed treatment with chondroitinase ABC promotes sensorimotor recovery and plasticity after stroke in aged rats. Brain 135. 1210-1223 (2012).
Hill, J. J. et al. Intracerebral chondroitinase ABC and heparan sulfate proteoglycan glypican improve outcome from chronic stroke in rats. Proceedings of the National Academy of Sciences 109. 9155-9160 (2012).
Dmitrieva, N. et al. Chondroitinase ABC I-Mediated Enhancement of Oncolytic Virus Spread and Antitumor Efficacy. Clinical Cancer Research 17. 1362-1372 (2011).
Tester, N. J. et al. Effect of Body Temperature on Chondroitinase ABC's Ability to Cleave Chondroitin Sulfate Glycosaminoglycans. Journal of Neuroscience Research 85. 1110-1118 (2007).
Lee, H. et al. Sustained delivery of thermostabilized chABC enhances axonal sprouting and functional recovery after spinal cord injury. Proceedings of the National Academy of Sciences 107. 3340-3345 (2010).
Kwon, B. K. et al. A Systematic Review of Directly Applied Biologic Therapies for Acute Spinal Cord Injury. Journal of Neurotrauma 28. 1589-1610 (2011).
Hyatt, A. J. T. et al., Controlled release of chondroitinace ABC from fibrin gel reduces the level of inhibitory glycosaminoglycan chains in lesioned spinal cord. Journal of Controlled Release 147. 24-29 (2010).
Rossi, F. et al. Sustained Delivery of Chondroitinase ABC from Hydrogel System. Journal of Functional Biomaterials 3. 199-208 (2012).
Smith, P. K. et al. Measurement of Protein Using Bicinchoninic Acid. Analytical Biochemistry 150. 76-85 (1985).
Huang, Y.-C. et al. Controlled release of chondroitinase ABC in chitosan-based scaffolds and PDLIA microspheres. Carbohydr Polym 84. 788-793 (2011).
Appel, E. A. et al. Sustained release of proteins from high water content supramolecular polymer hydrogels. Biomaterials 33. 4646-4652 (2012).
Stempfer, G. et al. A fusion protein designed for noncovalent immobilization stability, enzymatic activity, and use in an enzyme reactor. Nat Biotechnol 14. 481-484 (1996).
Wang, W. et al. Instability, stabilization, and formulation of liquid protein pharmaceuticals. International Journal of Pharmaceutics 185. 129-188 (1999).
Nakamura, S. et al. Controlled release of FGF-2 using fragmin/protamine microparticles and effect on neovascularization. Journal of Biomedical Materials Research Part A. 91A. 814-823. ( 2009).
Mort, J. S. et al. Measurement of Glycosaminoglycan Release from Cartilage Explants. Methods in Molecular Medicine vol. 135 Methods in Molecular Medicine (ed A. P. Cope) 201-209 (2007).
Liu, T. et al. Sustained release of neurotrophin-3 and chondroitinase ABC from electrospun collagen nanofiber scaffold for spinal cord injury repair. Journal of Biomedical Materials Research Part A 100A. 236-242 (2012).
Petsalaki, E. et al. Accurate Prediction of Peptide Binding Sites on Protein Surfaces. PLoS Comput Biol. 5(3). 1-10—(2009).
Lin, C-C. et al. Metal-chelating affinity hydrogels for sustained protein release. Journal of Biomedical Materials Research Part A. Wiley Periodicals. Inc. 954-964. (2007).
Lin, C-C. et al. Enhanced Protein Delivery from Photopolymerized Hydrogels Using a Pseudospecific Metal Chelating Ligand. Pharmaceutical Research. 23(3). 614-622. (2006).
Vulic, K.. et al. Tunable Growth Factor delivery from Injectable Hydrogels for Tissue Engineering. J. Am. Chem. Soc. 134. 882-885. (2012).
Meilander, Nancy J. et al, Ziats NP, Bellamkonda RV (2001), "Liipid-based microtubular drug delivery vehicles", Journal of Control Release, 71, pp. 141-152.

* cited by examiner

MC-Streptavidin synthesis:

EGF modification with 2-iminobiotin:

SEQUENCE LISTING

<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: Sequence derived from yeast actin patch kinase
<220> FEATURE:
<221> NAME/KEY: misc_feature
<222> LOCATION: (1)...(1)
<223> OTHER INFORMATION: Gly linked to methyl cellulose by
      3-maleimidopropionate
<220> FEATURE:
<221> NAME/KEY: misc_feature
<222> LOCATION: (4)...(15)
<223> OTHER INFORMATION: SH3-binding peptide

<400> SEQUENCE: 1

Gly Gly Gly Lys Pro Pro Val Val Lys Lys Pro His Tyr Leu Ser
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: Amino acids 4-20 derived from yeast actin patch
      kinase
<220> FEATURE:
<221> NAME/KEY: misc_feature
<222> LOCATION: (1)...(1)
<223> OTHER INFORMATION: Gly linked to methyl cellulose by
      3-maleimidopropionate
<220> FEATURE:
<221> NAME/KEY: misc_feature
<222> LOCATION: (4)...(20)
<223> OTHER INFORMATION: SH3-binding peptide

<400> SEQUENCE: 2

Gly Gly Gly Lys Lys Thr Lys Pro Thr Pro Pro Lys Pro Ser His
1               5                   10                  15

Leu Lys Pro Lys
            20

<210> SEQ ID NO 3
<211> LENGTH: 15
<212> TYPE: PRT
<213> ORGANISM: Artificial Sequence
<220> FEATURE:
<223> OTHER INFORMATION: Amino acids 4-15 derived from yeast actin patch
      kinase
<220> FEATURE:
<221> NAME/KEY: misc_feature
<222> LOCATION: (1)...(1)
<223> OTHER INFORMATION: Gly modified by linkage to
      3-maleimidopropionate
<220> FEATURE:
<221> NAME/KEY: misc_feature
<222> LOCATION: (4)...(15)
<223> OTHER INFORMATION: SH3-binding peptide

<400> SEQUENCE: 3

Gly Gly Gly Lys Pro Pro Val Val Lys Lys Pro His Tyr Leu Ser
1               5                   10                  15

<210> SEQ ID NO 4
<211> LENGTH: 20
<212> TYPE: PRT
<213> ORGANISM: Artificial Sequence
<220> FEATURE:

```
<223> OTHER INFORMATION: Amino acids 4-20 derived from yeast actin patch
      kinase
<220> FEATURE:
<221> NAME/KEY: misc_feature
<222> LOCATION: (1)...(1)
<223> OTHER INFORMATION: Gly modified by linkage to
      3-maleimidopropionate
<220> FEATURE:
<221> NAME/KEY: misc_feature
<222> LOCATION: (4)...(20)
<223> OTHER INFORMATION: SH3-binding peptide

<400> SEQUENCE: 4

Gly Gly Gly Lys Lys Thr Lys Pro Thr Pro Pro Lys Pro Ser His
1               5                   10                  15

Leu Lys Pro Lys
            20

<210> SEQ ID NO 5
<211> LENGTH: 15
<212> TYPE: PRT
<213> ORGANISM: Artificial Sequence
<220> FEATURE:
<223> OTHER INFORMATION: Amino acids 4-15 derived from yeast actin patch
      kinase
<220> FEATURE:
<221> NAME/KEY: misc_feature
<222> LOCATION: (4)...(15)
<223> OTHER INFORMATION: SH3-binding peptide

<400> SEQUENCE: 5

Gly Gly Gly Lys Pro Pro Val Val Lys Lys Pro His Tyr Leu Ser
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: SH3-binding peptide from yeast

<400> SEQUENCE: 6

Lys Pro Pro Val Val Lys Lys Pro His Tyr Leu Ser
1               5                   10

<210> SEQ ID NO 7
<211> LENGTH: 17
<212> TYPE: PRT
<213> ORGANISM: Artificial Sequence
<220> FEATURE:
<223> OTHER INFORMATION: SH3-binding peptide from yeast

<400> SEQUENCE: 7

Lys Lys Thr Lys Pro Thr Pro Pro Lys Pro Ser His Leu Lys Pro Lys
1               5                   10                  15

<210> SEQ ID NO 8
<211> LENGTH: 20
<212> TYPE: PRT
<213> ORGANISM: Artificial Sequence
<220> FEATURE:
<223> OTHER INFORMATION: Amino acids 4-20 derived from yeast actin patch
      kinase
<220> FEATURE:
<221> NAME/KEY: misc_feature
<222> LOCATION: (4)...(20)
<223> OTHER INFORMATION: SH3-binding peptide

<400> SEQUENCE: 8
```

```
Gly Gly Gly Lys Lys Thr Lys Pro Thr Pro Pro Pro Lys Pro Ser His
1               5                   10                  15

Leu Lys Pro Lys
            20

<210> SEQ ID NO 9
<211> LENGTH: 6
<212> TYPE: PRT
<213> ORGANISM: Artificial Sequence
<220> FEATURE:
<223> OTHER INFORMATION: tobacco etch virus cut site

<400> SEQUENCE: 9

Glu Asn Leu Tyr Phe Gln
1               5

<210> SEQ ID NO 10
<211> LENGTH: 16
<212> TYPE: PRT
<213> ORGANISM: Artificial Sequence
<220> FEATURE:
<223> OTHER INFORMATION: spacer

<400> SEQUENCE: 10

Glu Phe Pro Lys Pro Ser Thr Pro Pro Gly Ser Ser Gly Gly Ala Pro
1               5                   10                  15
```

AFFINITY-BASED CONTROLLED RELEASE SYSTEM

FIELD OF THE INVENTION

The invention relates to affinity-based release of therapeutic agents from a polymer wherein each of the therapeutic agent and polymer contain corresponding binding partners that through their reversible binding interaction control the release of the therapeutic agent from the polymer. The therapeutic agent includes biomolecules that influence cells or the cellular response both in vitro for cell culture and in vivo for therapeutic benefit, whether in animal or humans.

BACKGROUND

Many promising therapeutics are increasingly protein-based;[1-3] however, bioactive protein delivery remains a challenge.[4] Two main approaches have emerged to control protein release: (i) encapsulation in nano-/micro-particles, which provides a diffusive barrier and (ii) incorporation in affinity-based drug delivery systems, which establishes a dynamic equilibrium to delay release.[5,6] Although protein encapsulation is common, the harsh environments (organic solvents, aqueous/organic interfacial free energy, shear force, and lyophilization) present during the encapsulation process can diminish protein bioactivity and drug loading is generally low.[7,8] Affinity-based release systems overcome these limitations by sequestering proteins, commonly growth factors, in a polymer or polymer matrix, much like the extracellular matrix in vivo. These systems generally consist of a polymer (naturally occurring or synthetic and degradable, bioresorbable or biostable), such as a hydrogel, that has been chemically modified to bind a growth factor with moderate or high affinity, depending on the required rate of release, to attenuate the diffusional release of the protein.[6] For example, heparin or heparin-binding peptides have been immobilized to various matrices to deliver a variety of heparin-binding proteins;[9-18] however, this approach is inherently limited to heparin-binding proteins. Recombinant human basic fibroblast growth factor (rh-FGF2) binding peptide can be used to control the release of rhFGF2 from PEG hydrogels, yet is similarly limited to FGF2.[19] Collagen scaffolds have been shown to bind therapeutic fusion proteins that contain a collagen binding domain;[20] however, this system requires collagen as a scaffold and the rate of release cannot be tuned. A system which can deliver a diversity of therapeutic agents, including proteins, with a tunable rate of protein release is required.

SUMMARY

The invention includes a A composition comprising:
(a) a chimeric molecule comprising a biologically active molecule, and a first binding moiety covalently linked thereto; and
(b) a polymer comprising polymeric matrix having a second binding moiety, which specifically binds with the first binding moiety, covalently linked to the matrix, wherein the first and second binding moieties are reversibly bound to each other.

In embodiments, the composition is an extended release composition.

The first and second binding moieties reversibly bind with each other, and preferably form a complex having a dissociation constant $K_d$ of between $10^{-3}$ and $10^{-9}$.

According to one embodiment, the ratio of the second binding moiety to the first binding moiety in the composition is at least 10:1.

The polymeric matrix can comprise monomeric units, wherein, on average, each unit from which the matrix is produced includes between 0.25 and 3 functional groups capable of forming a covalent linkage with the second binding moiety from which the polymer is produced, and, on average, the fraction of said monomeric units of the polymeric matrix which form said covalent linkage with at least one said second binding moiety is between 1/50 and 1, inclusively.

The polymeric matrix can comprise monomeric units, wherein, on average, the polymer includes 1 second binding moiety covalently linked thereto per 1 to 100 monomeric units. Each of the monomeric unit covalently linked to a second binding moiety can have from 1 to 3 said second binding moieties covalently linked thereto. The polymeric matrix can comprise a hydroxyl-substituted polysaccharide having a degree of substitution (DS) of between $0.5 \leq DS \leq (N-0.2)$, wherein N is the total theoretical degree of substitution for a monomeric unit of the polymeric matrix, wherein said substituent is an alkyl group.

In a particular embodiment, the composition is a hydrogel, optionally a reverse thermal gelling polymer.

A composition wherein the binding domain of the protein is an SH3 binding domain is also described.

In embodiments in which the polymer is a derivative of cellulose e.g., methyl cellulose, hydroxyl groups of the cellulose can be carboxylated and said peptidyl ligand is covalently linked to the matrix by a carboxyl linkage.

In an embodiment, the forms a hydrogel in situ within i.e., less than 2 hours, more preferably within 90, 80, 70, 60, 50, 40, 30, 20, 10, 9, 8, 7, 6, 5, 4, 3, 2, 1 minute of injection into a mammal.

The hydrogel can have a shear storage modulus of at least 15 Pa at a temperature of 37° C.

The peptidyl ligand can include an amino acid sequence having a plurality of proline residues.

The polymer matrix can include an alkylated cellulose in which the alkyl group is methyl; ethyl; propyl; straight-chain or branched butyl, pentyl, hexyl, heptyl, octyl, nonyl or decyl; or any combination of the foregoing, and wherein the degree of substitution of the alkyl groups is between 0.9/3 and 1.7/3.

The invention includes a composition wherein a biologically active peptide comprises recombinant human basic fibroblast growth factor (rhFGF) or chondroitinase ABC (ChABC).

A hydrogel polymer defining the polymer matrix can have a critical gelation temperature of at least 25° C. to provide diffusion controlled in vivo release of the protein from the composition for a period of at least one week.

The composition can include an additional polymer such as hyaluronan.

In an embodiment, the invention is a syringe preloaded with a unit dose of a composition of the invention, as e.g., a hydrogel for injection.

The invention includes an injectable pharmaceutical composition comprising:
(a) a chimeric protein comprising an amino acid sequence comprising a biologically active peptide and a binding domain of a protein fused thereto; and
(b) an biocompatible injectable hydrogel polymer comprising a polymeric matrix having a peptidyl ligand covalently linked thereto, wherein the peptidyl ligand is reversibly bound to the binding domain to provide extended delivery of the protein to a subject for at least one week.

BRIEF DESCRIPTION OF FIGURES

Reference is made to the accompanying figures which illustrate aspects of the invention, and together with the remainder of the specification serve to explain the principles of the invention.

DETAILED DESCRIPTION

The inventors have created a versatile composition, than can be a gel, a hydrogel [or]. The composition provides extended release of a biological agent such as a protein.

An injectable, fast gelling blend of two polysaccharides, hyaluronan (HA) and methylcellulose (MC), provides minimally invasive, localized drug delivery to the injured spinal cord and brain.[21,22] Additionally, HAMC can be loaded with proteins to provide localized, diffusion-mediated release. Protein release from HAMC is complete within one to two days in vitro;[23,24] however, factors must often be available for longer times to elicit functional recovery.[25,26] Thus, extending the protein release profile of this therapeutic drug delivery matrix would improve administration of an exciting new class of drugs.

Figure 2:
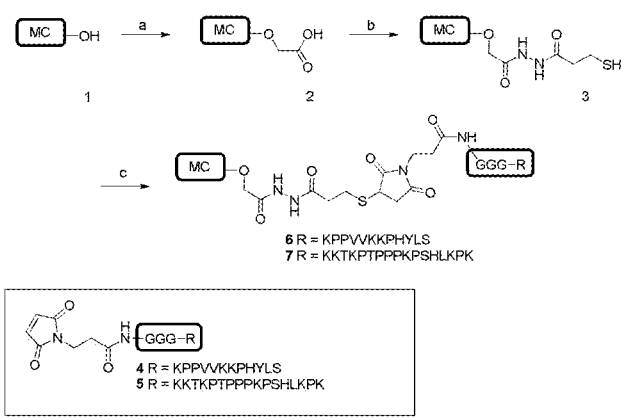
FIG. 2 shows the synthetic scheme for obtaining methyl cellulose-peptide, MC-GGGKPPVVKKPHYLS (SEQ ID NO: 1) and MC-GGGKKTKPTPPPKPSHLKPK (SEQ ID NO: 2) via 3-maleimidopropionic-GGGKPPVVKKPHYLS (SEQ ID NO: 3) and 3-maleimidopropionic-GGGKKTKPT-PPPKPSHLKPK (SEQ ID NO: 4). Reagents are a) 3M bromoacetic acid, 1M NaOH, 3 h, 4° C. b) (i) EDC, 3,3'-dithiobis(propionic dihydrazide), pH 4.5, 2 h, rt. (ii) DTT, pH 8.5, 24 h, rt. c) 4 or 5, PBS, pH 6.8, $N_2$ (g), 24 h, rt.
Figure 3:
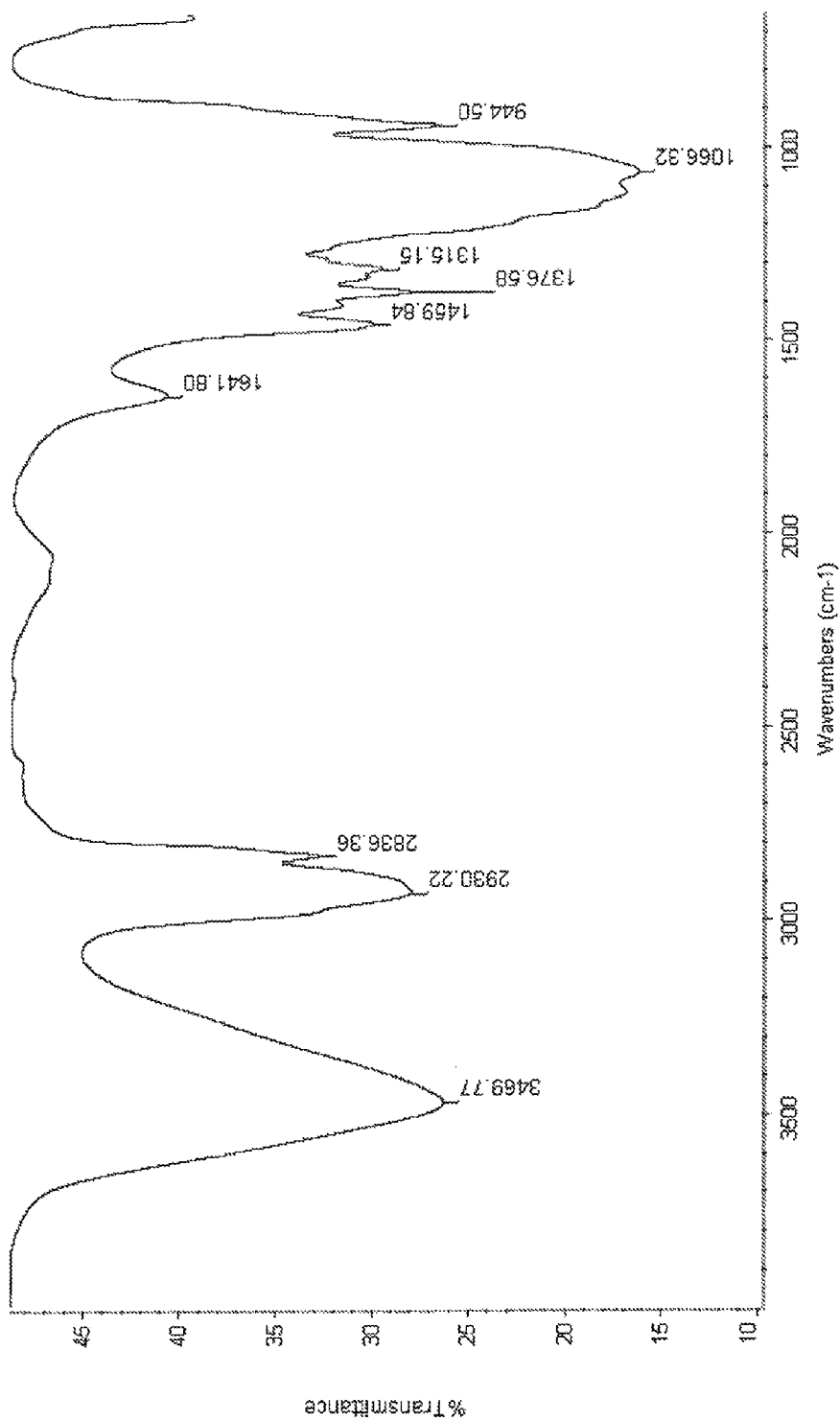
FIG. 3 shows FT-IR characterization of A) MC, B) MC-$CO_2$H, and C) MC-SH. In B), new O—H stretches (3400-3600 $cm^{-1}$) and new C=O stretch (~1600 $cm^{-1}$) are highlighted. In C), the S—H stretch (~2300 $cm^{-1}$) is highlighted. This stretch is more evident in D) the spectral subtraction of A) MC from C) MC-SH.
Figure 3B:
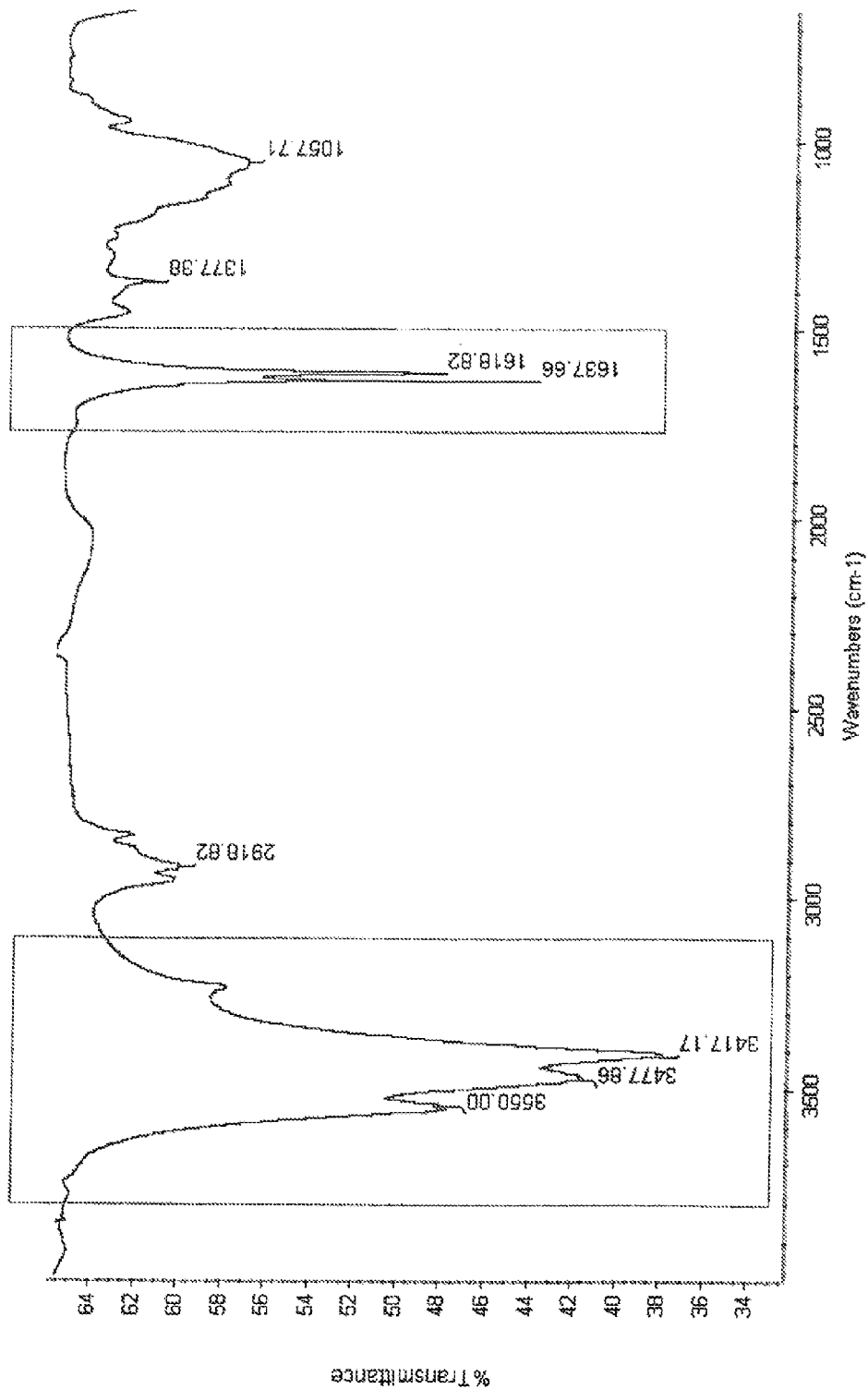
Figure 3C:
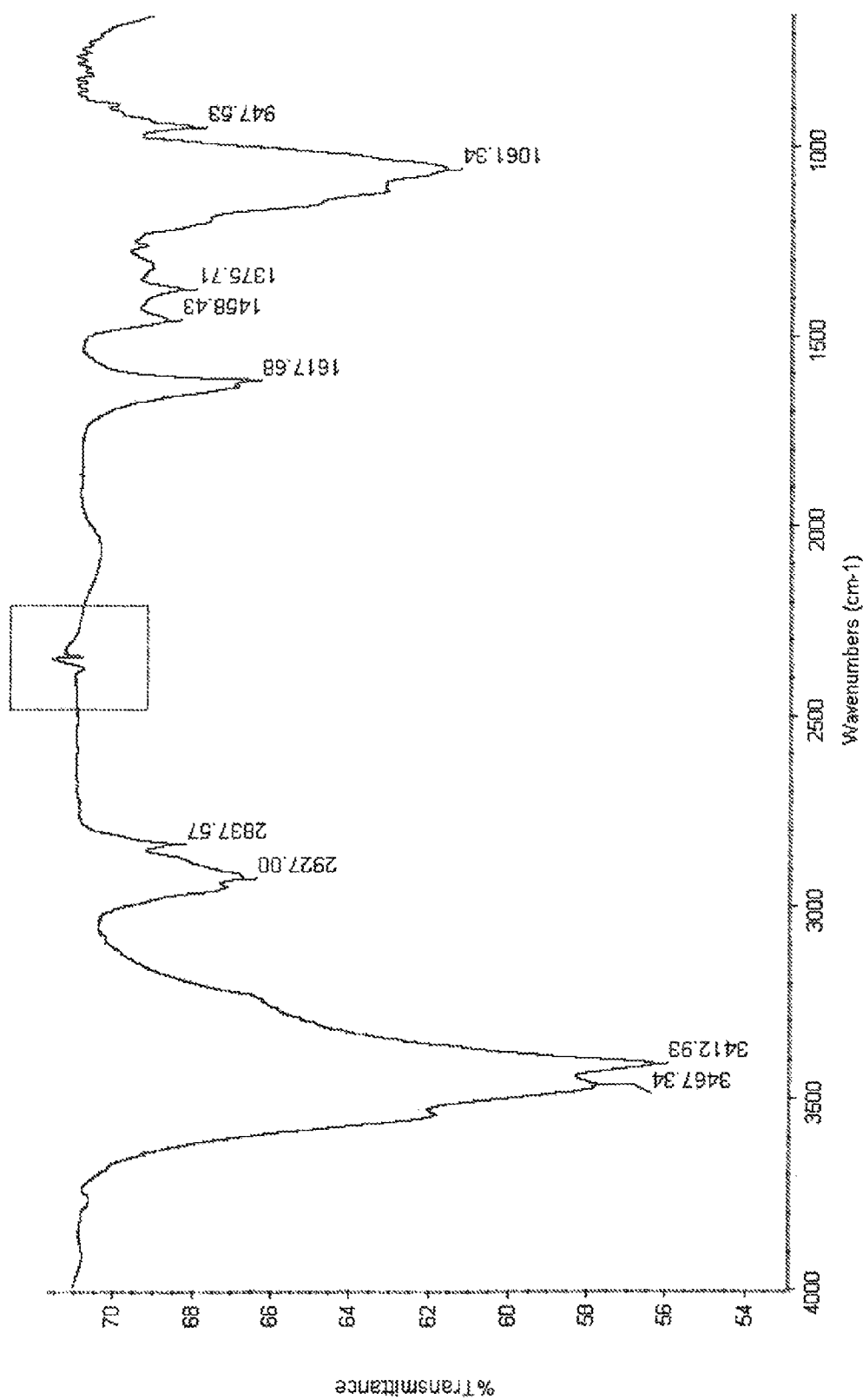
Figure 3D:
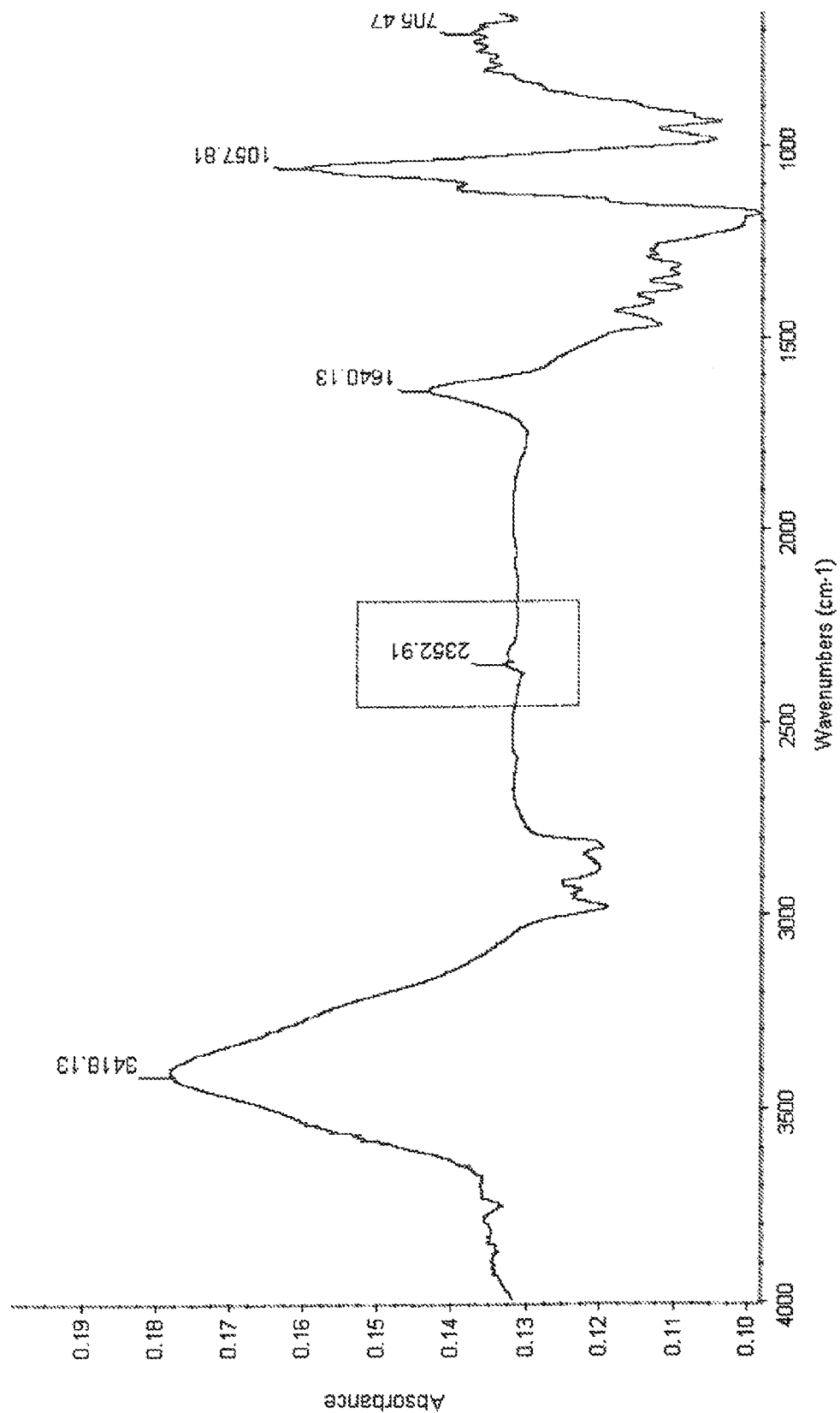

Here, a composition that permits minimally invasive and localized delivery of therapeutic proteins with tunable and extended release profiles. HAMC was used as a drug delivery matrix. The delivery of rhFGF2 was used because it is a neuroprotective, angiogenic factor that requires at least five days of continuous delivery to achieve tissue and functional benefit in rat models of spinal cord injury.[27] To achieve sustained release of this protein from the HAMC hydrogel, rhFGF2 was expressed in *Escherichia coli* (*E. coli*) as a fusion protein with Src homology 3 domain (SH3), (SH3-rhFGF2, FIG. 1) and MC was modified with one of two SH3-binding peptides (See the scheme of FIG. 2). Specifically, chemical modification of methyl cellulose, MC (1), a reverse thermal gelling polymer, was achieved starting with a Williamson ether synthesis[28] to produce carboxylated MC 2. This was then coupled with 3,3'-dithiobis(propionic dihydrazide)[29] using 1-ethyl-3-[3-(dimethylamino)propyl] carbodiimide (EDC), followed by disulfide reduction with dithiothreitol (DTT) to yield thiolated MC 3 (scheme of FIG. 2, FIG. 3). Thiolated MC was reacted with 3-maleimidopropionic-SH3-binding peptide (4,5) via a Michael addition to afford MC-SH3-binding peptide (MC-peptide) 6 or 7 i.e., a polymer matrix having a SH3-binding peptide covalently linked thereto as a binding moiety. The MC-SH3-binding peptide was combined with unmodified HA to form HAMC-peptide. HA decreases the gelation temperature of MC, resulting in a fast gelling polymer that is also easily injectable through a fine needle due to the shear-thinning property of HA.[21]

Figure 1:
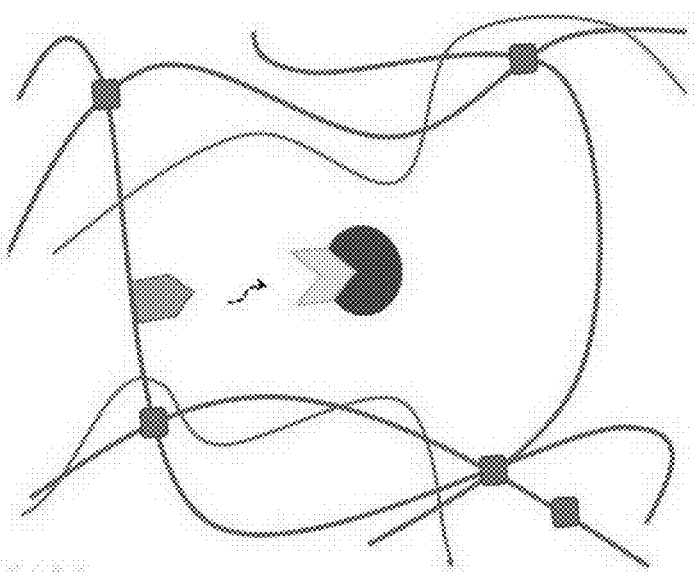
FIG. 1 shows controlled release of SH3-rhFGF2 from hydrogels modified with SH3-binding peptides. Transient association between SH3-binding peptides covalently bound to methyl cellulose and the SH3 protein modulate release of the fusion protein SH3-rhFGF2 from the matrix.

SH3 has previously been shown to bind to various proline-rich peptide sequences with different affinities ($K_d$) ranging from $10^{-5}$ to $10^{-7}$ M.[30] Two different SH3-binding peptides with varying affinity to SH3 (4, $K_d=2.7\times10^{-5}$M or 5, $K_d=2.7\times10^{-7}$ M) were tested in our system as a way to control release. As shown in FIG. 1, it was hypothesized that transient interactions between the binding pairs would slow the diffusion of SH3-rhFGF2 from the matrix. Thus, the rate of release could be tuned by either changing the concentration of the binding peptide, or by using binding peptides with different affinities, where peptides with stronger affinities would further attenuate release.

MC was modified with one of two peptides that have different binding affinities to SH3: KPPVVKKPHYLS ((SEQ ID NO: 6) weak binder, 4, Kd=2.7x10-5M) and KKTKPTPPPKPSHLKPK (SEQ ID NO: 7) strong binder, 5, Kd=2.7x10-7M).30 Three glycine residues were incorporated at the N-terminus of the SH3-binding peptide to facilitate protein-peptide recognition and binding once the peptide was covalently attached to the MC hydrogel. This spacer minimizes possible steric hindrance that may affect binding interactions of immobilized ligands with the corresponding protein.19 A substitution rate of 1 SH3-binding peptide per 15 monomer units, or 180-200 μmol peptide/g MC (FIG. 4) was consistently achieved for each peptide. MC-peptide (3 wt %) was then simply blended with HA (1 wt %) to form a physical hydrogel blend of HAMC-peptide.

Figure 5:
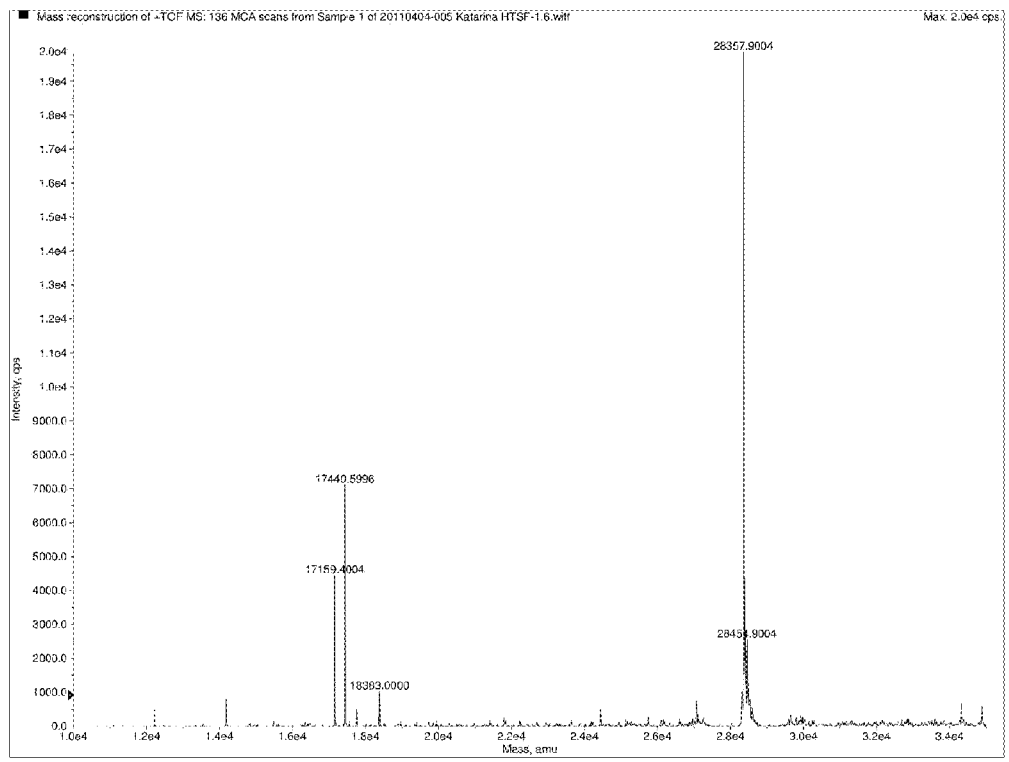
FIG. 5 shows ESI protein mass spectrum of SH3-rhFGF2 (computer predicted mass 27.7 kg/mol). M+ found 28.4 kg/mol (salts bound to M+ account for the shift in molecular weight).
Figure 6:
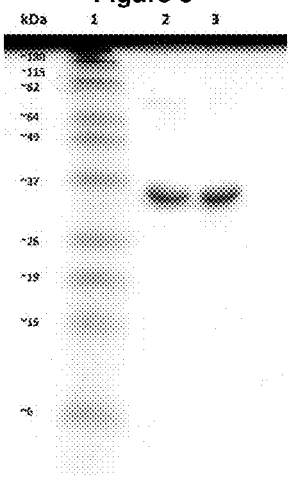
FIG. 6 shows SDS-PAGE characterization of SH3-rh-FGF2 shows that it is has the predicted and stable molar mass over a 4 month storage period. Lane 1) Ladder; 2) SH3-rhFGF2 (MW27.6 kDa); 3) SH3-rhFGF2 (stored for 4 months at −80° C.).
Figure 7:
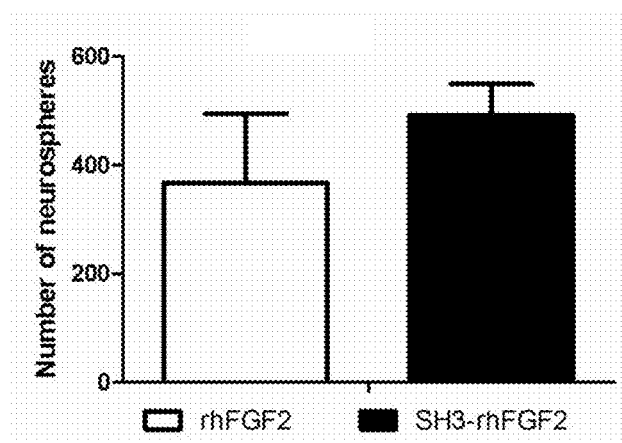
FIG. 7 shows bioactivity of SH3-rhFGF2 is equivalent to that of commercial rhFGF2 using a neurosphere assay and identical concentrations of rhFGF2 (10 ng/mL). No statistical significance between groups ($p>0.05$).

A bifunctional fusion protein of SH3 and rhFGF2 was designed to include a small linker region between SH3 and rhFGF2 that acts as a hinge to ensure each protein will fold correctly and function as it does in its native state.[31] While the SH3 domain can be bound at either the N- or C-terminus of the fusion protein, it was bound at the N-terminus of rhFGF2 to maintain bioactivity. The fusion protein was expressed in BL21 *E. coli* and purified via a hexahistidine tag using a nickel affinity column. The fusion protein was characterized by mass spectrometry (FIG. 5) and denaturing gel electrophoresis (FIG. 6). To confirm the rhFGF2 portion of the fusion protein was still bioactive, a cell survival assay using mouse-derived neural stem progenitor cells was performed.[32] The activity of the fusion protein was identical to that of commercial rhFGF2 (p>0.05), indicating that bioactivity was preserved in the fusion protein (FIG. 7).

Figure 8:
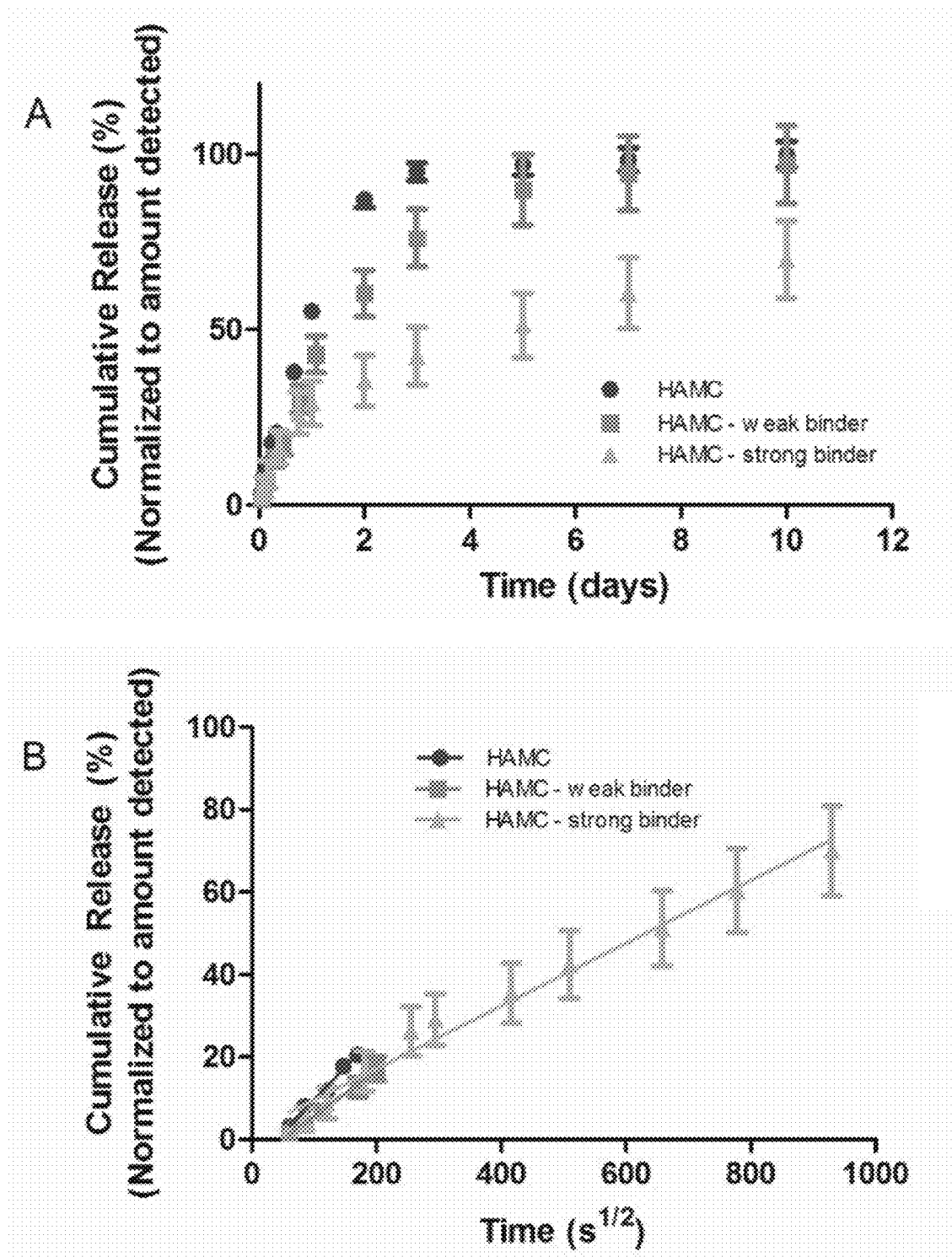
FIG. 8 shows. A) In vitro release profile of SH3-rhFGF2 delivered from HAMC, HAMC-weak binder and HAMC-strong binder hydrogels normalized to total amount of protein detected. Protein release from HAMC-weak binder is slower than from HAMC for the first 3 days of release ($p<0.01$), after which there is no difference in the amount of protein released. Protein release from HAMC-strong binder is slower than HAMC ($p<0.005$) and HAMC-weak binder ($p<0.05$) after the first 24 h of release. B) The slope of SH3-rhFGF2 release from HAMC, HAMC-weak binder and HAMC-strong binder against the square root of time is representative of Fickian diffusion coefficients for each gel ($p<0.001$ between all groups). Diffusion-controlled release is sustained for 8 hours from HAMC, 12 hours from HAMC-weak binder and for 10 days from HAMC-strong binder. The non-zero intercept indicates that swelling affected diffusion at the early timepoints. (n=4, mean±standard deviation are plotted).

Release of SH3-rhFGF2 (20 μM) was investigated in vitro under conditions that mimic the in vivo environment of the spinal cord. Artificial cerebrospinal fluid with 0.2 mg/mL heparin was used as a release buffer, and was added to tubes containing HAMC and HAMC-peptide (188 μmol peptide/g MC) hydrogels. Tubes were placed on an oscillatory shaker at 37° C. and release buffer was completely removed and replaced with fresh buffer at multiple timepoints. Release samples were frozen at −20° C. until protein was assayed by enzyme-linked immunosorbent assay (ELISA). Data are presented as cumulative protein release (relative to initial protein loaded) as a function of time. Data normalized to total amount of protein detected are shown in FIG. 8.

Figure 9:
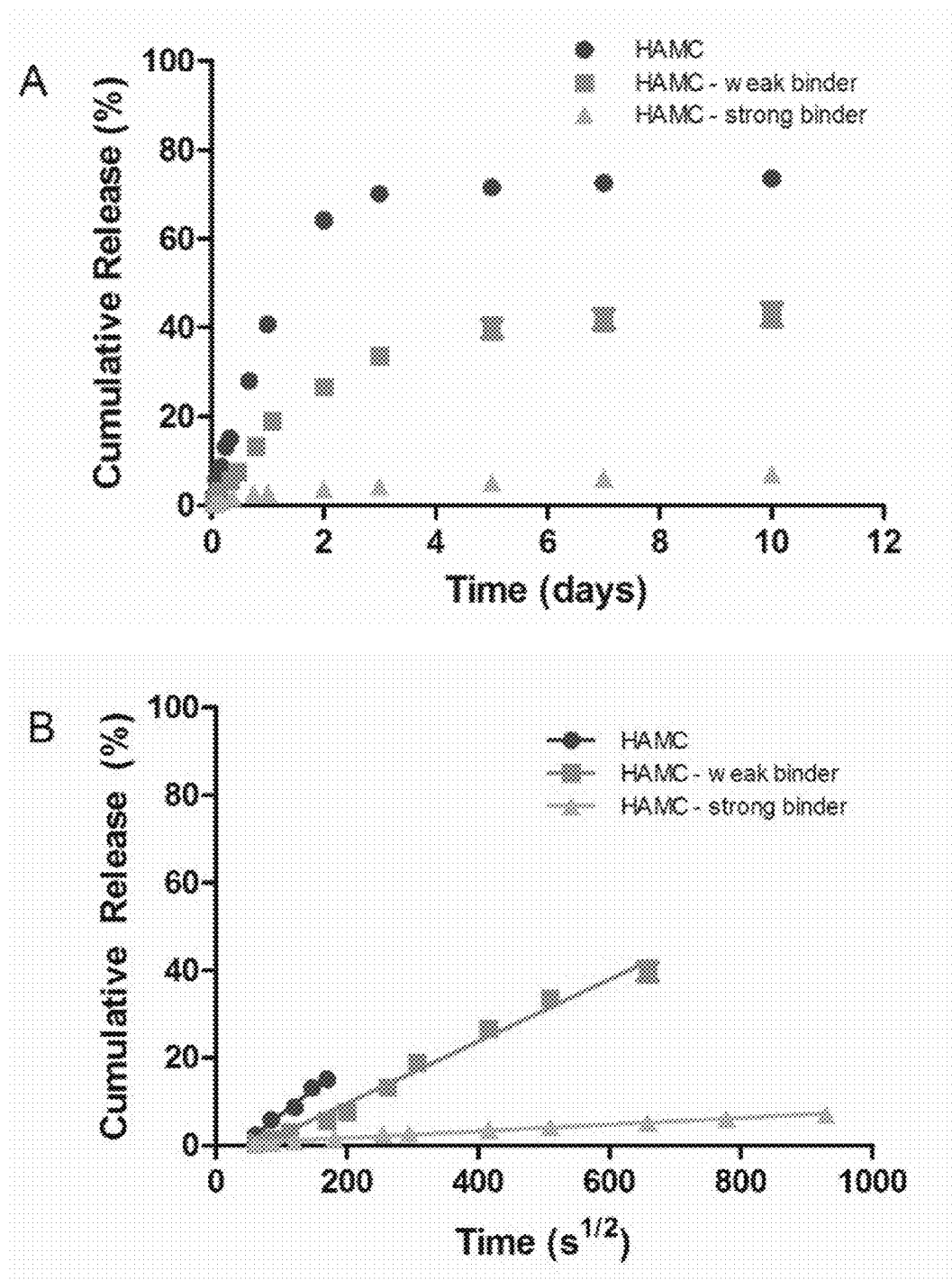
FIG. 9 shows A) In vitro release profile of SH3-rhFGF2 delivered from HAMC, HAMC-weak binder and HAMC strong binder hydrogels. SH3-binding peptides attenuate release such that different release profiles are achieved. $p<0.001$ for all groups, except between HAMC-weak binder and HAMC-strong binder at t=1 and 2 h where $p<0.05$. B) The slope of SH3-rhFGF2 release from HAMC, HAMC-weak binder and HAMC-strong binder against the square root of time is representative of Fickian diffusion coefficients for each gel ($p<0.001$ between all groups). Furthermore, diffusion-controlled release is sustained for 5 days from HAMC-weak binder and for 10 days from HAMC-strong binder. The non-zero intercept indicates that swelling affected diffusion at the early timepoints. Cumulative release (%) is calculated relative to amount of protein loaded. (n=4, mean±standard deviation are plotted).

Release of SH3-rhFGF2 from HAMC alone was nearly complete at two days whereas release from HAMC-peptide hydrogels (HAMC-weak binder and HAMC-strong binder) extended to more than 10 days (FIG. 9A).

The fastest release was obtained from HAMC, followed by HAMC-weak binder, and HAMC-strong binder and was statistically significant between all groups (p<0.001) except between HAMC-weak binder and HAMC-strong binder at t=1 and 2 h (p<0.05). This confirms the hypothesis that tunable release profiles are achieved by changing the affinity of the binding peptide.

To investigate differences in the diffusion coefficient of SH3-rhFGF2 in the three hydrogels, the fractional protein release was plotted against the square root of time ($t^{1/2}$, FIG. 9B). In this plot, a linear relationship is indicative of Fickian diffusion.[33] By comparing the slopes in the linear region for each hydrogel, it was determined that the relative diffusion coefficient for SH3-rhFGF2 was significantly different for each gel (p<0.001). For HAMC alone, the data fit linearly for the first 8 hours of release, similar to published data for diffusional release of immunoglobulin G and α-chymotrypsin from HAMC.[23] Notably, for HAMC-weak binder and HAMC-strong binder the data fit linearly for 5 and 10 days of release respectively. This shows that release from HAMC-peptide hydrogels, which is sustained for a 10 day period, is still mediated by Fickian diffusion. Protein release from HAMC-peptide hydrogels that is linear avoids the burst and biphasic release often observed in encapsulated drug delivery systems.[34] Since HAMC hydrogels have been shown to be stable in vitro for over 28 days,[23] neither polymer degradation nor dissolution was expected to affect the release profile. Thus, immobilizing SH3-binding peptides to HAMC confers the ability to tune the rate of diffusion-controlled release of SH3 fusion proteins.

The release profile for a drug can have a dramatic effect on the effectiveness of the therapy. Consequently, a priority of drug delivery system design is to allow tunable release rates. Herein, we showed that the release of a therapeutic fusion protein can be controlled through physical binding interactions with a biomaterial matrix. Protein release was found to be linear and is tunable.

Figure 10:
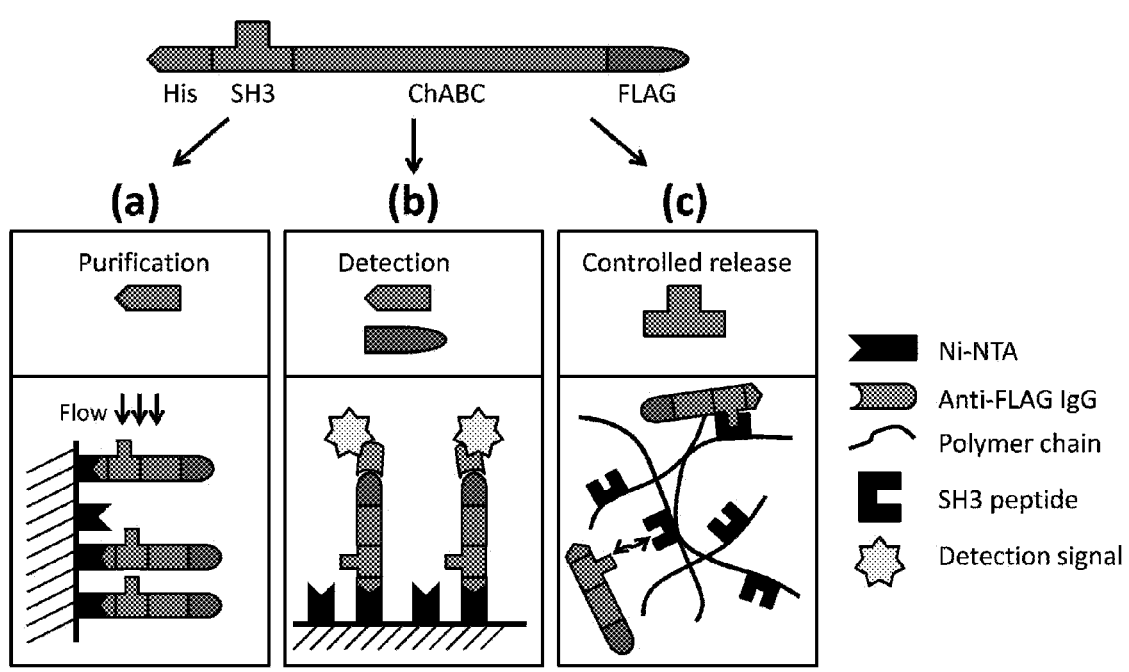
FIG. 10 shows a protein construct and corresponding material pair provide a complete purification, detection, and controlled release platform. The chosen therapeutic protein is recombinantly expressed as a fusion with Src homology domain 3 (SH3), an N-terminal His tag, and a C-terminal FLAG tag. This construct is used for protein purification, detection and, controlled release without reference to the chosen therapeutic protein. (a) Purification using a nickel affinity column that reversibly binds the His tag. (b) Detection using an ELISA where the protein is bound to a 96-well plate coated with Ni-NTA via the His tag and quantified using an antibody against the FLAG tag that is coupled with HRP. (c) Controlled release using an SH3-peptide modified polymeric hydrogel. The reversible binding of the SH3 and SH3-peptide slows the diffusion of the protein from the hydrogel.

In a second demonstration of the feasibility of this approach, the protein of interest was recombinantly expressed as a fusion protein with Src homology domain 3 (SH3), an N-terminal histidine (His) tag, and a C-terminal FLAG tag. The His tag enables purification by a nickel (Ni) affinity column while the His and FLAG tags allow detection by ELISA. The SH3 protein binds orthogonally and reversibly with its binding peptides[30] and was used to control release from a polymer covalently modified with an SH3 binding peptide (FIG. 10). Release rates are then easily tunable by choosing peptides with various dissociation constants, for example, $K_d$ between $10^{-5}$ to $10^{-7}$ M, or by modulating the matrix-binding peptide to protein ratio.

Chondroitinase ABC (ChABC) was used to construct a methyl cellulose (MC) polymeric hydrogel covalently modified with an SH3-binding peptide (MC-peptide). Methylcellulose is safe for local delivery to the injured spinal cord[21,35]. ChABC is a bacterial enzyme having an ability to degrade chondroitin sulfate proteoglycans (CSPG) for treatment of spinal cord injury[1], and more recently, diseases of the eye[36,37], stroke[38,39], and cancer[40]. As a large, 131 kDa, thermally unstable[41,42] protein, ChABC should be delivered to the injury site over a period of at least one week to show efficacy[43]. Previous controlled release studies of ChABC did not quantify the amount of enzyme released, and relied on qualitative activity data combined with release of model proteins to verify delivery profiles[42,43-46].

ChABC was recombinantly expressed as His-SH3-ChABC-FLAG in *E. coli*, hereafter referred to as ChABC-SH3. Purification was achieved using a Ni affinity column followed by size exclusion chromatography. The purified protein appeared as a single band on an SDS-PAGE gel (FIG. 11a) and its activity was verified by measuring the rate at which it degraded chondroitin sulfate A (CS-A). The recombinant protein construct was found to be more robust than a commercially available enzyme after one freeze-thaw cycle (FIG. 11b), allowing ChABC-SH3 to be stored at −80° C. for many months without loss in activity.

Figure 11:
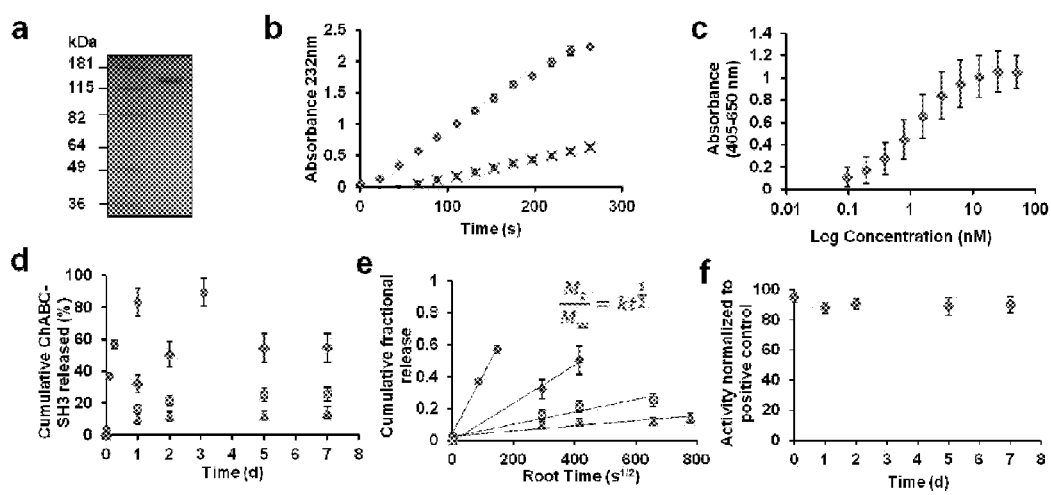
FIG. 11 shows application of the complete detection and controlled release platform to recombinant Chondroitinase ABC-SH3 fusion (ChABC-SH3). (a) SDS-PAGE of purified recombinant ChABC-SH3 (MW=131 kDa) showed only a single band. (b) Kinetic ChABC activity assay showed that our ChABC-SH3 (♦) is more active than commercially available ChABC (x) after one freeze thaw cycle (n=3, mean±s.d). (c) His/FLAG double tag ELISA for ChABC-SH3 showed high reproducibility and linear range from 0.1 nM to 10 nM (n=15, mean±s.d). (d) Cumulative release profiles of ChABC released from unmodified MC hydrogel (●) or MC-peptide hydrogels. MC was modified with weak binding SH3 peptide ($K_d=10^{-5}$ M) and used at 100-fold excess (♦) or 300-fold (▲) excess to ChABC-SH3 or a strong binding SH3 peptide ($K_d=10^{-7}$ M) at 100-fold excess to ChABC-SH3 (■) (n=3, mean±cumulative s.d). (e) Release profiles fit to a short time approximation for unidirectional diffusion from a plane sheet[29] showed that release was tunable by changing the peptide binding strength used (weak binder 100× vs. strong binder 100×, $p<0.01$) or by changing the peptide to protein ratio within the gel (MC vs. weak binder 100× vs. weak binder 300×, $p<0.001$) (n=3, mean±cumulative s.d). (f) Released ChABC-SH3 was active for at least 7 days (results shown for strong binder 100×, n=3, mean±s.d).
Figure 12:
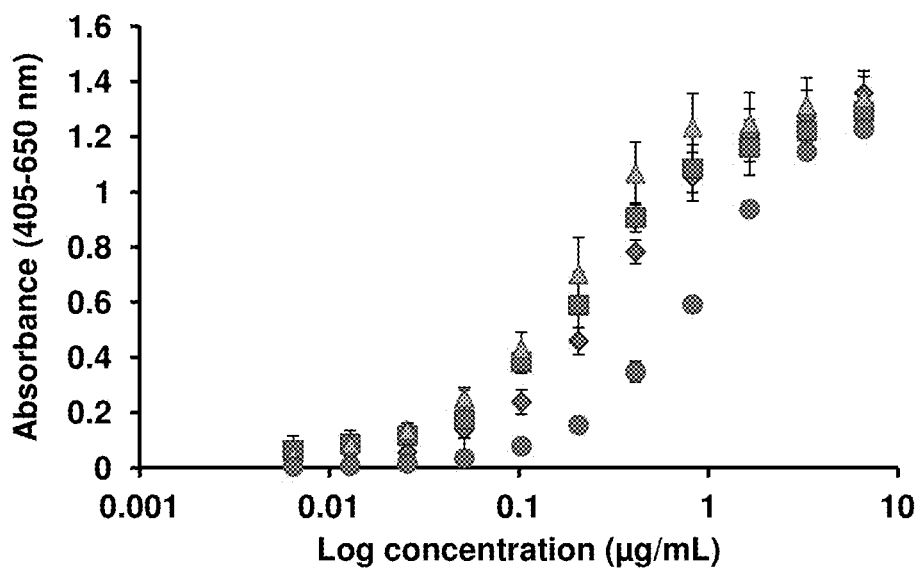
FIG. 12 shows His/FLAG double tag ELISA for ChABC-SH3 is specific to ChABC-SH3 with 0 (♦), 10 (■), 100 (▲), or 1000× (●) molar excess of BSA. (n=3, mean±s.d.).

Detection of ChABC was achieved using a His/FLAG double tag ELISA system where the His tag binds to a Ni-nitriloacetic acid (NTA)-coated 96 well plate and an anti-FLAG antibody is used for quantification. The resulting standard curve had a lower limit of quantification (LOQ) of 0.1 nM, corresponding to a mass concentration of 13 ng/mL (FIG. 11c). This is significantly more sensitive than other techniques for detection of proteins like ChABC where there is no antibody available: it is one order of magnitude more sensitive than the microplate format of the NanoOrange protein assay (Invitrogen); two orders of magnitude more sensitive than the microplate format of the microBCA protein assay[47]; three orders of magnitude more sensitive than absorbance at 280 nM; and four orders of magnitude more sensitive than the microplate format of the Bradford protein assay[48]. Moreover, the assay was found to retain its specificity for ChABC-SH3 (FIG. 12) and because the two tags responsible for detection are on opposite ends of the protein, this method detects only intact protein so will at least reduce false positives if protein fragments are present.

Figure 13:
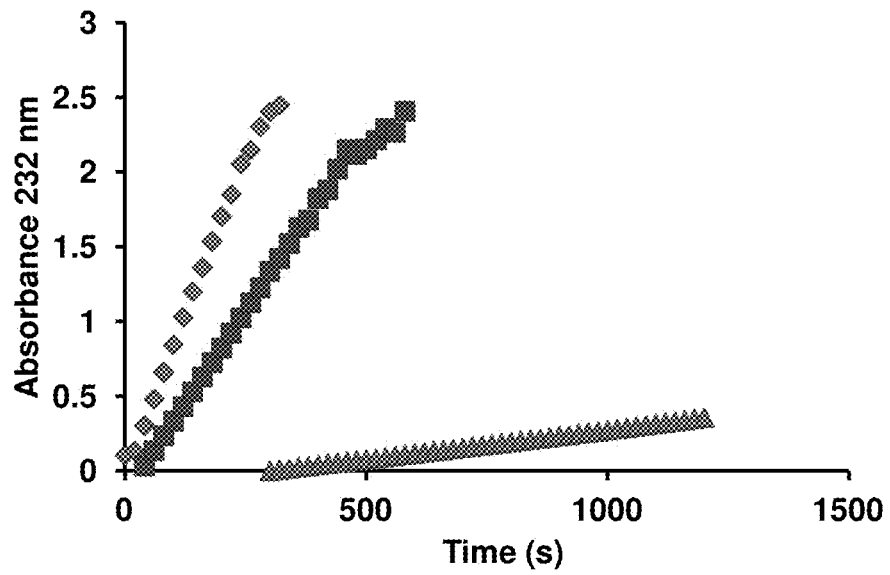
FIG. 13 illustrates thermal instability of ChABC. ChABC-SH3 solutions were incubated in artificial cerebrospinal fluid (aCSF) at 37° C. for 0 (♦), 24 (■) or 48 (▲) h. Activity was measured using a kinetic activity assay that measured the degradation of chondroitin sulfate A (CS-A). 95% of ChABC activity is lost in 48 h.
Figure 14:
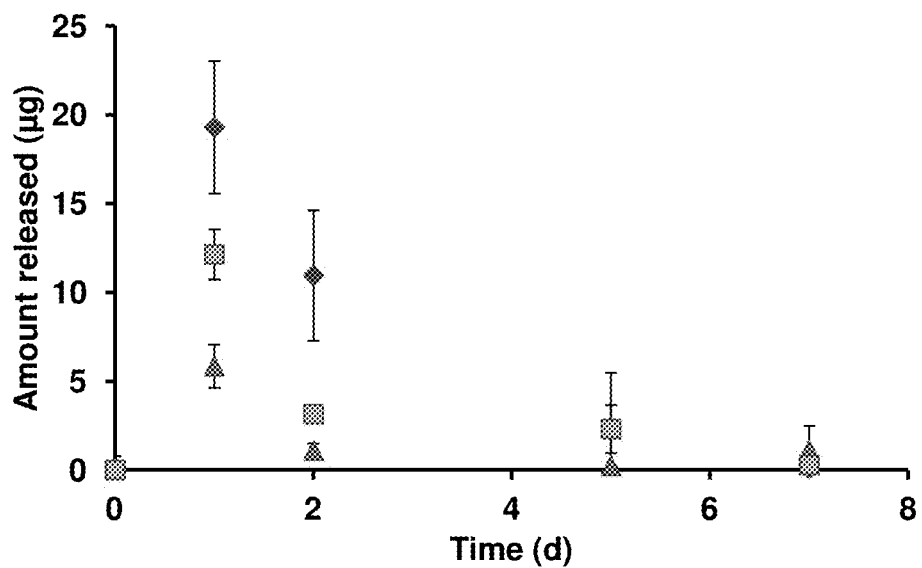
FIG. 14 shows the amount of ChABC-SH3 released as a function of time from an MC hydrogel modified with weak binding SH3 peptide ($K_d=2.7\times10^{-5}$ M) at 100× excess to ChABC-SH3 (♦), weak binding SH3 peptide at 300× excess to ChABC-SH3 (▲), and strong binding SH3 peptide ($K_d=2.7\times10^{-7}$ M) at 100× excess to ChABC-SH3 (■). Although the majority of ChABC-SH3 is released on days 1 and 2, measurable amounts of protein are still released at days 5 and 7.
Figure 15:
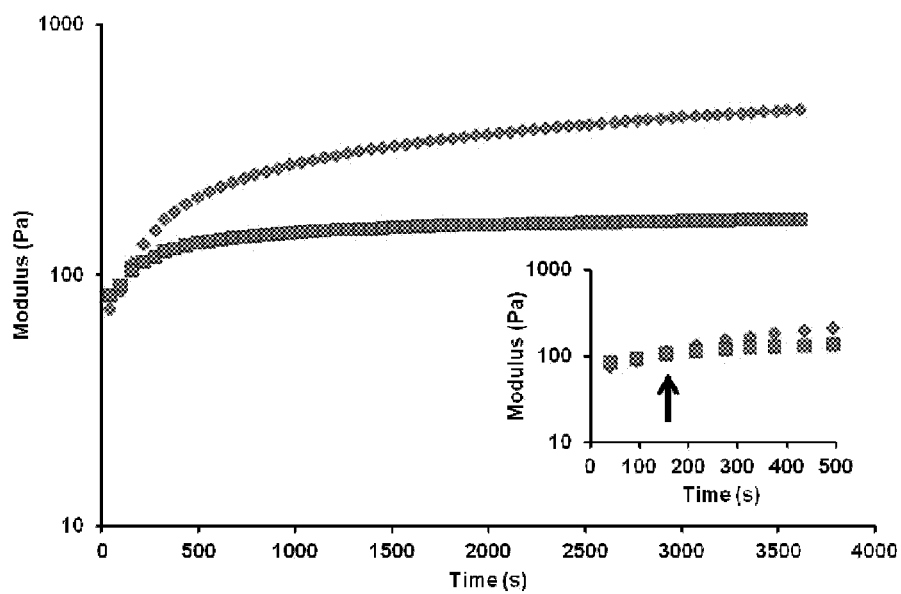
FIG. 15 shows MC-peptide hydrogel gelling within 4 min at 37° C. The storage (G', ♦) and loss moduli (G", ■) of the hydrogel were determined as a function of time on an AR-1000 rheometer fitted with a 40 mm, 2° cone and plate geometry. An amplitude sweep was performed to confirm that the frequency and strain were within the linear viscoelastic region. Temperature was equilibrated at 4° C. using the integrated Peltier plate and sample evaporation was minimized using a solvent trap. The temperature was then changed to 37° C. at time 0 and the storage and loss moduli measured every minute for one hour at 1 Hz and 1% strain. Gelation is defined as when G'>G" which occurs approximately 4 min after the temperature was increased to 37° C. (n=3, mean±s.d). Inset shows a zoom-in of the crossing point.

The affinity based MC-peptide hydrogel system was able to release active ChABC-SH3 for at least 7 days (FIG. 11d, 11e, 11f). Without the hydrogel, incubating ChABC-SH3 at 37° C. resulted in a 95% loss in activity over 48 h (FIG. 13), indicating a protective effect of the hydrogel on the protein. Protein polymer interactions in hydrogels have previously been shown to retain native protein structure and maintain activity[49], and enzyme stabilization by immobilization is a well known industrial technique[50]. Additionally, the release profile from this system was tunable either by controlling the SH3/SH3-peptide binding constant (i.e., a strong binder with a $K_d=10^{-7}$ M was compared to a weak binder with a $K_d=10^{-5}$ M) or by changing the ratio of SH3-peptide to ChABC-SH3 within the gel i.e., a 100 times excess of SH3-binding peptide to ChABC-SH3 protein was compared to a 300 times excess (FIG. 11d). When fit to a short time approximation for unidirectional diffusion from a plane sheet[33], the slope, indicative of the apparent diffusivity of the protein from the gel, was significantly decreased by increasing the SH3 matrix-bound peptide excess or by increasing the SH3 peptide binding strength (FIG. 2e). As with many protein release experiments, 100% of the protein was not accounted for. This may be due to protein aggregating and precipitating over time[51] causing the plateau phase in the release profiles. Despite this plateau, however, measurable amounts of ChABC-SH3 were still released at days 5 and 7 (FIG. 14) and released ChABC remained bioactive throughout the release period.

Figure 16:
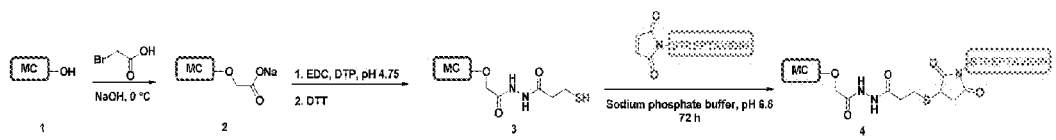
FIG. 16 shows a scheme for synthesis of MC-streptavidin and EGF modification with 2-iminobiotin.
Figure 16:
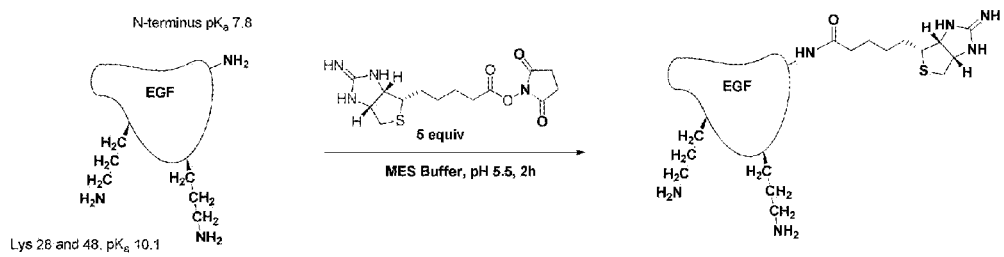

Streptavidin binds 2-iminobiotin with medium affinity, $K_d$ 12.5 μM (Reznik, G. O. et al. *Proc. Natl. Acad. Sci. USA*. 1998. 95, 13525). According, MC can be with streptavidin and EGF with 1 iminobiotin group as shown in the schemes of FIG. 16. In such embodiment, any protein having reactive amine (N-terminus or primary amino group of lysine) can be modified by covalent linkage using NHS-activated 2-iminobiotin. The iminobiotinylated protein is purified from unmodified protein using streptavidin affinity chromatography. Protein modification is confirmed using mass spectrometry. The amount of streptavidin conjugated to MC can be quantified using amino acid analysis.

Figure 17:
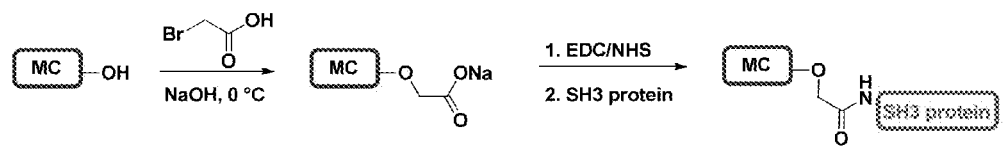
FIG. 17 shows a scheme for covalent linkage of MC and SH3 protein.

It is also possible to covalently link a binding domain of the SH3 protein or the entire SH3 protein to MC and modify a therapeutic by covalent linkage to an SH3 binding peptide. In the case the agent being a therapeutic protein or polypeptide the SH3 protein or domain and the agent can be expressed together, similar to that described above for SH3-rhFGF2. See the scheme of FIG. 17.

For in vitro applications, the affinity binding pairs can be used to influence cell fate in culture conditions. For example, tissue culture polystyrene can be modified one of the binding partners and the correspondingly modified therapeutic agent can be temporarily immobilized through an affinity interaction. The resulting media conditions will have the therapeutic agent diffuse into its aqueous solution over time based on the reversible binding of the binding partners on each of the therapeutic and polymer. The same is true for other materials used in culture, including glass and other polymers, whether synthetic or naturally-derived and whether biostable, bioresorbable or biodegradable. The described approach to control release is applicable to many polymers that can be covalently modified to include a binding moiety.

Polymers suitable for use as part of a composition of the invention may be biodegradable, bioerodible or biostable, formed for use as an injectable or a preformed structure. These include scaffolds, micropsheres, nanospheres; with a variety of porosities from nanoporous to microporous to macroporous. Polymers can be for in use in in vivo and/or in vitro applications. Polymers can be use as part of a controlled release vehicle, whether in vitro or in vivo, and can for use with cells for in vitro culture or with cells for in vivo or to influence the cell phenotype. A polymer can be modified with a binding partner either on the surface or throughout the bulk, depending on the ultimate application.

Suitable biocompatible, non-biodegradable and degradable polymers include both synthetic and naturally occurring polymers, as blends or copolymers of any/all of the polymers listed, but are not limited to: polyacrylates; ethylene-vinyl acetates; acyl substituted cellulose acetates; non-degradable polyurethanes; polystyrenes; polyvinyl chlorides; polyvinyl fluorides; poly(vinyl imidazoles); chlorosulphonate polyolefins; polyethylene oxides; poly(propylene oxides); poly(ethylene), poly(propylene); cellulose or derivatives thereof; polyesters, poly(alpha hydroxyl esters), poly(lactide), poly(glycolide), copolymers of lactide and glycolide, polyhydroxybutyrate, polycaprolactone, copolymers of lactic acid and lactone, copolymers of lactic acid and poly(ethylene glycol), copolymers of α-hydroxy acids and α-amino acids (polydepsipeptides), poly(peptides), polyanhydrides, polyorthoesters, polyphosphazenes, copolymers of hydroxybutyrate and hydroxyvalerate, poly ethylene carbonate), copoly(ethylene carbonate), polyethyleneterephthalate or mixtures of these polymers. Examples of resorbable/biodegradable polymers are lactide homopolymers poly(L-lactide), poly(D,L-lactide), and copolymers of lactide and glycolide such as 50:50 poly(DL lactide co-glycolide) (PLG). polycarbonates, degradable polyurethanes, poly(ortho esterds), poly(dioxanone), hyaluronan or derivatives thereof, methyl cellulose or derivatives thereof, alginate, chitosan, agarose, copolymers of PEG with poly(lactic acid), oligomers of poly(lactic acid), lactides, copolymers of PEG and amino acids, conjugates of PEG with polysaccharides for example a conjugate produced from dextran and polyoxyethylene-glycol monomethyl ether.

The polymeric carrier matrix of the disclosed systems can be a biocompatible matrix as is generally known in the art. For instance, in one embodiment, the carrier matrix can be a single-phase biocompatible carrier matrix. Moreover, the carrier matrix can be either a homogeneous matrix or a heterogeneous matrix, as desired.

In one embodiment, the carrier matrix can be hydrophilic in nature. This can be preferred when utilizing the invention in an aqueous-based system, for example in a clinical setting, as a hydrophilic matrix can be less likely to provoke an immuno-suppression response to the matrix by a patient. This is not a requirement of the invention, however, and in other embodiments, the carrier matrix can be a hydrophobic polymeric matrix.

In one embodiment of the invention, the carrier matrix is a hydrogel. For instance, the carrier matrix can be a biocompatible hydrogel. Hydrogels are herein defined to include polymeric matrices that can be highly hydrated. Suitable hydrogel matrices can include crosslinked hydrogels. In addition, crosslinked hydrogel carrier matrices of the invention can optionally be degradable when utilized in an aqueous environment. For example, in one embodiment, the carrier matrix can include a cross-linked hydrogel including a hydrolyzable cross-linking agent, such as polylactic acid, and can be degradable in an aqueous environment.

Hydrogel carrier matrices of the present invention can include natural polymers such as glycosaminoglycans, polysaccharides, proteins, polypeptides and the like, as well as synthetic polymers, as are generally known in the art. A non-limiting list of hydrophilic polymeric materials that can be utilized in forming hydrogels of the present invention can include dextran, hyaluronic acid, chitin, heparin, collagen, elastin, keratin, albumin, polymers and copolymers of lactic acid or glycolic acid with poly(ethylene glycol), methyl cellulose, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

In a preferred embodiment, the hydrogel is methyl cellulose having hydroxyl groups to which binding moieties have been covalently linked. The degree of substitution (DS) of the polymer is about 1.7/3 prior to such modification to include the binding moiety.

Hydrogel matrices of the present invention can be formed according to any method as is generally known in the art. For instance, the hydrogel can self-assemble upon mere contact of the various components or upon contact in conjunction with the presence of particular external conditions (such as temperature or pH). Alternatively, assembly can be induced according to any known method following mixing of the components. For example, step-wise or chain polymerization of multifunctional monomers or macromers can be induced via photopolymerization, temperature dependent polymerization, and/or chemically activated polymerization. Optionally, the hydrogel can be polymerized in the presence of an initiator. For example, in one embodiment, the hydrogel can be photopolymerized in the presence of a suitable initiator such as Irgacure® or Darocur® photoinitiators available from Ciba Specialty Chemicals. In another embodiment, a cationic initiator can be present. For example, a polyvalent elemental cation such as $Ca^{2+}$, $Mg^{2+}$, Al$^{3+}$, La$^{3+}$, or Mn$^{2+}$ can be used. In another embodiment, a polycationic polypeptide such as polylysine or polyarginine can be utilized as an initiator.

The components of the carrier matrix can also be designed so as to provide a self-assembling carrier matrix. For example, a hydrogel precursor can be administered to a patient, and the hydrogel matrix can self-assemble at physiological conditions following administration of the precursor. For instance, the hydrogel precursor can include self-assembling biopolymers such as collagens, laminins, proelastin peptides, and the like. Optionally, a self-assembling hydrogel precursor can include synthetic polymers that can array themselves according to domains, as is generally known in the art. For example, hydrophilic, relatively charge-neutral synthetic polypeptides such as polyglycine can be modified to function in this capacity. Polypeptides can be crosslinked by using carboxy-activating crosslinking agents such as water-soluble carbodiimides. Such crosslinking agents can be used to attach self-assembling proteins or other self-assembling macromolecules to the polypeptides. One example of this approach includes formation of a carbodiimide linkage of collagen or laminin with polylysine. Other hydroxylated entities can be linked in a similar manner. For example, in one embodiment, polyvinyl alcohol can be linked with polypeptides using an epoxy-activation approach or crosslinked via polymerizable methacrylate groups along its side chains, as is known in the art.

In another embodiment, a self-assembling hydrogel can be generated by use of precursors that have been derivatized to contain favorably reactive groups. For example, a hydrogel of this type could be assembled using a first precursor derivatized with a particular reactive moiety and a second precursor derivatized with or comprising a second moiety that can preferentially react with the first moiety on the first precursor. Likewise, other such hydrogels could be generated using such reactive pairs wherein the two moieties that react to form the bond are each conjugated to the same or a different type of polymer.

In other embodiments the carrier matrix need not be a self-assembling matrix. For example, in other embodiments a hydrogel matrix for use in vivo can be administered to a patient according to a suitable administration method (e.g., orally or percutaneously) following assembly of the hydrogel. In other embodiments of the invention, the disclosed systems can be utilized in ex vivo applications, for example in tissue engineering applications, and as such, the carrier matrix of the invention need not be a self-assembling matrix.

The carrier matrix can be a highly porous matrix. For example, a hydrogel can be formed with mesh size, $\xi$, much larger than the size of the biologically active agent to be carried and delivered by the system. More specifically, the initial mesh size of a degradable matrix, or the constant mesh size of a non-degradable matrix, can be considerably larger than the size of the biologically active agent to be carried by and delivered from the matrix. For example, in one embodiment, the mesh size of a hydrogel carrier can be large enough to allow free diffusion of a macromolecular protein therapeutic agent through the hydrogel. In one particular embodiment, the carrier matrix can be formed to have a mesh size, $\xi$, between about 5 and about 50 nm.

The carrier matrix can be formed to have a mesh size that is smaller than the ligand/drug complex and yet larger than the drug itself. According to this particular embodiment, the drug can be held within the matrix through purely physical constraints as long as it is associated with a binding moiety of the polymer matrix, and can become free to diffuse through the matrix upon dissociation of the drug from the binding moiety. Any particular mesh size is not a requirement of the present invention, however, and the selection of any particular mesh size can generally depend at least in part upon the size of the biologically active materials to be delivered by the system.

The methylcellulose hydrogel used in the foregoing examples has an advantage as it is injectable through a 30 gauge needle and is thermally-inverse gelling, allowing in situ gellation at 37° C. This can thus provide a minimally invasive, localized, and sustained release strategy for therapeutic protein delivery.

Advantageously, a pair of binding moieties is selected to reversibly bind specifically with each other. In the context of this invention, "specific" means that the polymer-bound moiety binds preferentially to its counterpart linked to the biologically active portion of the chimeric molecule. While there may be non-specific interactions between the polymer and the chimeric molecule, the release is controlled predominantly by the affinity (or dissociation constant, $K_d$) between the binding partners covalently linked to the polymer and chimeric molecule, respectively. In the case of multiple therapeutic agents, binding pairs can be advantageously selected for each agent such that each binding pair is specific of other component(s) of the composition. In the case of peptide binding moieties, suitable pairs can be chosen given the teachings of Petsalki et al. (Petsalaki, E.; Stark, A.; Garcia-Urdiales, E.; Russell, R. B. *PLoS Comput Biol* 2009, 5(3), e1000335), the contents of which are incorporated herein by reference, and where the active agent is a polypeptide or protein, the matrix-bound binding moiety would be selected so as to bind specifically with the binding partner, but to have no significant binding with that portion of that polypeptide or protein that is not the binding partner.

Non-limiting examples of the therapeutic agents include, but are not limited to the group of therapeutic agents comprising anaesthetics for use in caudal, epidural, inhalation, injectable, retrobulbar, and spinal applications; analgesics, selected from the group comprising acetaminophen, baclofen, ibuprofen, fluriprofen, ketoprofen, voltaren, phenacetin and salicylamide; anti-inflammatories selected from the group comprising naproxen and indomethacin; antihistamines, selected from the group comprising chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussives selected from the group comprising dextromethorphan hydrobromide and guaifenesin; expectorants; decongestants, selected from the group comprising phenylephrine hydrochloride, phenylpropanolamine hydrochloride, pseudoephedrine hydrochloride, and ephedrine; antibiotics selected from the group comprising amebicides, broad and medium spectrum, fungal medications, monobactams and viral agents; bronchodilators selected from the group comprising theophylline, albuterol and terbutaline; cardiovascular preparations selected from the group comprising diltiazem, propranolol, nifedepine, clonidine, alpha adrenoceptor agonists, alpha receptor blocking agents, alpha and beta receptor blocking agents, antiotensin converting enzyme inhibitors, beta blocking agents, calcium channel blockers, and cardiac glycosides; central nervous system drugs selected from the group comprising thioridazine, diazepam, meclizine, ergoloid mesylates, chlorpromazine, carbidopa and levodopa; metal salts selected from the group comprising potassium chloride and lithium carbonate; minerals selected from the group consisting of iron, chromium, molybdenum and potassium; immunomodulators; immunosuppressives selected from the group comprising minocycline, cyclosporine A; thyroid preparations selected from the group comprising synthetic thyroid hormone, and thyroxine sodium; peptide and glycoprotein hormones and analogues selected from the group comprising human chorionic gonadotrophin (HCG), corticotrophin, human growth hormone (HGH—Somatotrophin) and erythropoietin (EPO); steroids and hormones selected from the group comprising ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, GM1 ganglioside, cAMP, and others; vitamins selected from the group comprising water-soluble vitamins and veterinary formulations; growth factors selected from the group comprising EGF, FGF2 and neurotrophin; peptides, peptide mimetics and other protein preparations; DNA; and, small interfering RNAs; with or without a pharmaceutically acceptable carrier or preservative.

An extended release composition can optionally include multiple therapeutics and these can be modified with the same or different binding partner(s) and their release from a composition independently controlled, as desired. This can achieve the same release profile for multiple therapeutics if they are modified with the same binding peptide partner or different release profiles if the therapeutics were modified with different binding peptide partners. Alternatively, the polymer could be modified with different binding partners and the therapeutic modified with the corresponding partners to each of these. With different affinities, the release profiles of the therapeutics would be different.

Disclosed systems and methods can thus be beneficially utilized for release of multiple drugs at independently controlled rates from a single carrier matrix. For example, according to this particular embodiment, two or more drugs are immobilized into a single composition by incorporating the same or different binding moieties that show specific interactions with corresponding binding moieties of the drug molecules. Release of each drug can then be determined and controlled by the strength of the specific interactions of the paired binding moieties and the concentration of matrix-bound moiety displaying that interaction, and release of the different agents can thus be controlled independently.

Relative concentrations of differing matrix-bound moieties in a composition can be controlled, for example, by preparing each modified polymer bearing a binding moiety separately from the other modified polymers and combining the modified polymers in appropriate amounts.

The affinity-based drug delivery vehicle of this invention has multiple applications and may be delivered via injection, transdermal, oral, sub-cutaneous, intranasal, vaginal, buccal, intrathecal, subdural, epidural, ocular space, dental, intratumoral, intramuscular, intraarticular, and intraveneously. The drug delivery vehicle can be injected into a fluid-filled (or partially-filled) cavity. These include all cavities throughout the body, including but not limited to the intrathecal space, the intra-articular cavity, among others.

In vitro release includes chemical modification of tissue culture polystyrene or other materials often used in cell culture, including glass, unmodified polystyrene or other suitable polymers, including those for 3D cell culture.

Abbreviations

SH3, Src homology 3 domain; rhFGF2, recombinant human basic fibroblast growth factor; HA, hyaluronan; MC, methyl cellulose; EDC, 1-ethyl-3-[3-(dimethylamino)propyl]carbodiimide; DTT, dithiothreitol; MC-peptide, methyl cellulose covalently modified with a SH3-binding peptide; HAMC-weak binder, MC modified with peptide GGGKP-PVVKKPHYLS (SEQ ID NO: 5) and blended with hyaluronan; HAMC-strong binder, MC modified with peptide GGGKKTKPTPPPKPSHLKPK (SEQ ID NO: 8) and blended with hyaluronan; ELISA, enzyme-linked immunosorbent assay.

Materials and Methods 3-maleimidopropionic acid was purchased from TCI America (Portland, USA). pET28 vector was purchased from Invitrogen (Burlington, Canada). Cloning of SH3-rhFGF2 fusion protein was done by GenScript (Piscataway, USA). Sodium hyaluronate of 2600 kg/mol was purchased from Lifecore (Chaska, USA). Methyl cellulose of 300 kg/mol (DS=1.7/3) was purchased from Shin Etsu (Tokyo, Japan). Sandwich ELISA kit for rhFGF2 was purchased from Peprotech (Rocky Hill, USA). All buffers were made with distilled and deionized water (dH$_2$O) prepared using a Millipore Milli-RO 10 Plus and Milli-Q UF Plus at 18 MΩ resistance (Millipore, Bedford, USA). Artificial cerebrospinal fluid (aCSF) was prepared as previously described.[35] All other solvents and reagents were purchased from Sigma-Aldrich and used as received. All FT-IR spectra were obtained using a Spectrum 1000 FT-IR spectrometer (Waltham, Mass.), collecting 32 scans in the 400-4000 cm$^{-1}$ range with a resolution of 2 cm$^{-1}$. Restriction enzymes were purchased from New England Biolabs (Pickering, ON). Anti-FLAG antibody was purchased from Abcam (Cambridge, USA).

Synthesis and Characterization

Synthesis of Carboxylated Methyl Cellulose (MC-CO$_2$H) 2

Methyl cellulose (2 g, 4% w/v) was dissolved in dH$_2$O (50 mL) and chilled to 4° C. Sodium hydroxide (6 g, 150 mmol, 3 M) and bromoacetic acid (6.95 g, 50 mmol, 1 M) were added and the solution stirred for 3 h at 4° C. The reaction was stopped by adding 0.4% NaH$_2$PO$_4$ and was neutralized to pH 7 by addition of 3 M HCl. The solution was dialyzed (MWCO 12-14 kDa, Spectrum Labs) against 0.2 M NaCl for 2 d, changing the dialysis buffer frequently during the first 24 h. The product was lyophilized (Labonco, Kansas City, USA) and characterized using FT-IR spectroscopy.

Synthesis of Thiolated Methyl Cellulose (MC-SH) 3

MC-CO$_2$H 2 (1 g, 0.25% w/v) was dissolved in dH$_2$O, pH 4.5 (200 mL) at 4° C. Once dissolved, the solution was warmed to room temperature and 1-ethyl-3-[3-(dimethylamino)propyl]carbodiimide (EDC, 958 mg, 5 mmol) and 3,3'-dithiobis(propionic dihydrazide) (DTP, 1.19 g, 5 mmol) were added sequentially with stirring. The pH of the reaction was monitored to ensure it remained at pH 4.5. After stirring for 2 h the reaction was stopped with addition of 1 M NaOH to pH 7. Dithiothreitol (DTT) (5 g, 32.5 mmol) was added and the pH of the solution was raised to pH 8.5 by addition of 1 M NaOH. After stirring for 24 h, the solution was acidified to pH 3.5 by addition of 3M HCl and dialyzed (MWCO 12-14 kDa, Spectrum Labs) against 100 mM NaCl, pH 3.5 for 3 d, changing the dialysis buffer frequently in the first 24 h. The solution was lyophilized and the product was characterized by FT-IR spectroscopy. Thiol concentration (expressed per gram MC) was quantified using the Ellman method.

Synthesis of 3-maleimidopropionic-SH3-Binding Peptides (4 and 5).

SH3-binding peptide on resin (China Peptides, Shanghai, China) was washed into an ISOLUTE column reservoir (Biotage, Charlotte, USA) with dichloromethane (DCM) and dried. 3-maleimidopropionic acid (338 mg, 2 mmol) and N,N'-diisopropylcarbodiimide (2.0 mL, 8 mmol) were stirred in DCM for 30 min under $N_{2(g)}$. The mixture was filtered and the filtrate was added to dry SH3-binding peptide on resin (0.2 mmol SH3-binding peptide), and reacted for 2 h with stirring. The resin was washed with DCM, methanol and 2-propanol sequentially using an ISO-LUTE column and dried under vacuum. The peptide was deprotected and cleaved from resin by reacting with 95% TFA (10 mL) with stirring for 2 h. The solution was filtered and the filtrate was collected in a round bottomed flask and TFA was evaporated. Crude peptide was precipitated in cold diethyl ether and purified by reverse-phase HPLC (Shimazdu, Japan) with a Phenomenex C18 250×10 mm column. Peptide purity was confirmed by ESI mass spectrometry (ABI/Sciex Qstar mass spectrometer).

Synthesis of SH3-Binding Peptide Modified Methyl Cellulose (MC-Peptide 6 and 7)

Figure 4:
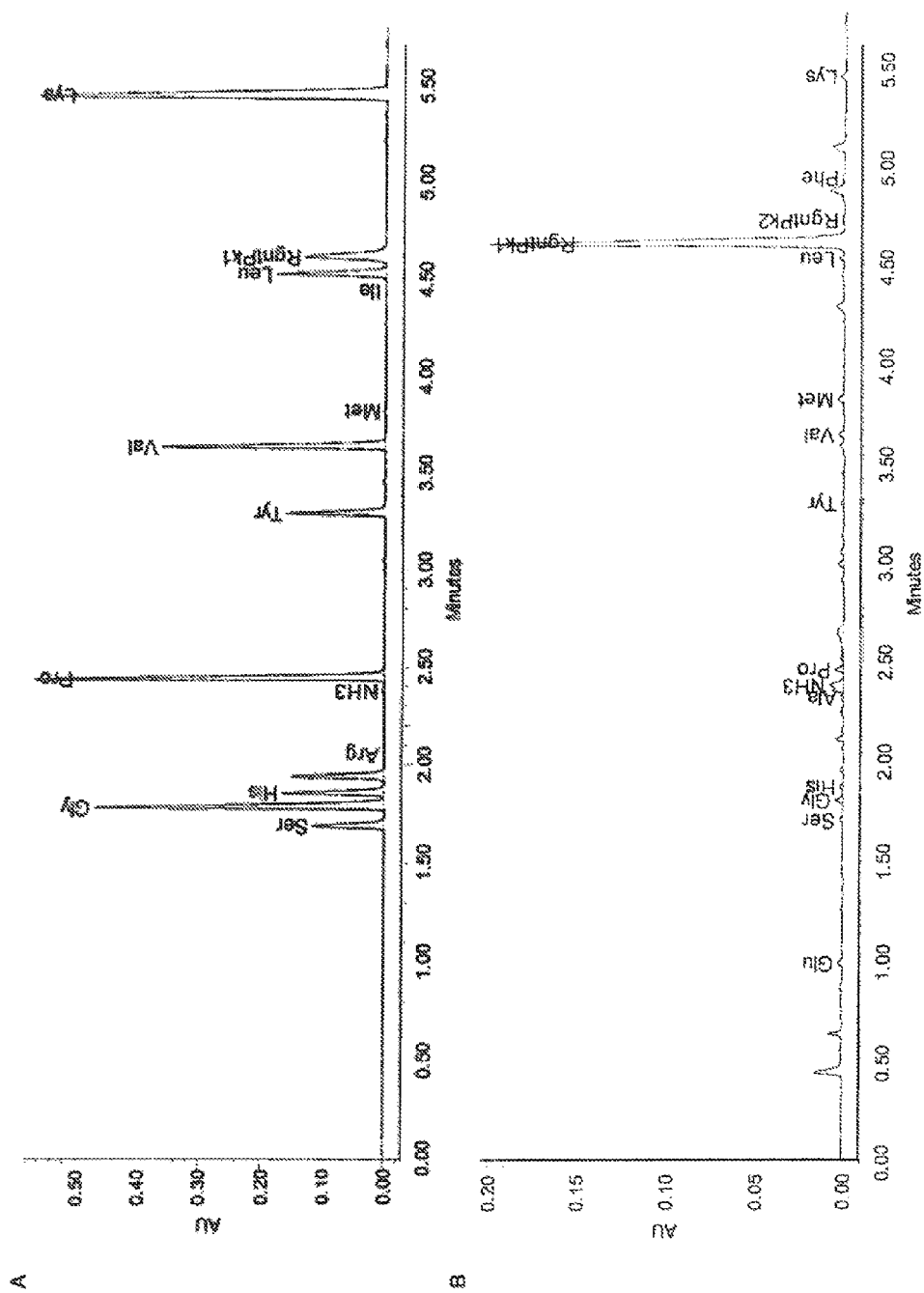
FIG. 4 shows amino acid analysis of the product of MC-SH 3 reacted with A) 3-maleimidopropionic-GGGKP-PVVKKPHYLS (SEQ ID NO: 3) and B) GGGKPPVVK-KPHYLS ((SEQ ID NO: 5) control SH3-binding peptide). A known amount of SH3-binding peptide dissolved in MC was used as a standard, peak areas were calculated for each amino acid. The concentration of SH3-binding peptide was A) 188 μmol/g MC and B) 0.69 μmol/g MC, demonstrating successful immobilization of the SH3-binding peptide to MC-SH in (A).

MC-GGGKPPVVKKPHYLS (SEQ ID NO: 1) and MC-GGGKKTKPTPPPKPSHLKPK (SEQ ID NO: 2) were synthesized. MC-SH (300 mg, 1% w/v, 0.012 mmol thiols) was dissolved in degassed PBS (pH 6.8, 30 mL) at 4° C. The solution was purged intermittently for 15 min with $N_2(g)$. 3-maleimidopropionic-GGGKPPVVKKPHYLS (SEQ ID NO: 3) (102 mg, 0.059 mmol) was added and the reaction was stirred under $N_2(g)$, in the dark for 24 h. The reaction was dialyzed (MWCO 8 kDa, Spectrum Labs) for 48 h against PBS, pH 4 and then against $dH_2O$ for 24 h. The product MC-GGGKPPVVKKPHYLS (6) (SEQ ID NO: 1) was lyophilized and characterized by amino acid analysis (Pico-tag system, Waters Corporation). The identical synthesis was followed for MC-GGGKKTKPTPPPKPSHLKPK (7) (SEQ ID NO: 2) with 3-maleimidopropionic-GGGKKTKPTPPPKPSHLKPK (SEQ ID NO: 4) (133 mg, 0.059 mmol). The identical synthesis was followed for control reactions using SH3-binding peptide alone instead of 3-maleimidopropionic-SH3-binding peptide: GGGKPPVVKKPHYLS (SEQ ID NO: 5) and GGGKKTKPTPPPKPSHLKPK (SEQ ID NO: 8). Control SH3-binding peptides were used to confirm the Michael addition between 3-maleimidopropionic-SH3-binding peptide and thiolated MC (FIG. 4).

Expression and Purification of SH3-rhFGF2

A plasmid was purchased from Genscript, which coded for a fusion protein with a hexahistidine tag at the N-terminus, followed by a tobacco etch virus cut site (ENLYFQ (SEQ ID NO: 9)), Src homology 3 domain (SH3), a spacer (EFPKPSTPPGSSGGAP)31 (SEQ ID NO: 10), and rhFGF2 (C78S, C96S) at the C-terminus in a pET28a(+) plasmid. The SH3-rhFGF2 plasmid was transformed into BL21 (DE3) Escherichia coli (E. coli) and expressed. A starting culture of 20 mL LB with 50 µg/mL of kanamycin was shaken overnight at 37° C., and then transferred into a 1.8 L solution of terrific broth, 50 µg/ml of kanamycin and 6 drops of anti-foam 204. The culture was placed in a 37° C. water bath with an air bubbler until an OD600 of 0.8 when 1.8 mL of 190 mg/mL of IPTG was added and the protein was expressed for 5 h at 37° C. The bacterial pellet was collected by centrifugation at 12,227 g (Beckman coulter centrifuge Avanti J-26 with rotor JLA-8.1000) for 10 min at 4° C. and re-suspended in binding buffer (50 mM Tris pH 7.5, 500 mM NaCl, 5 mM imidazole) to a total volume of 60 mL. The sample was divided into 2 vials of 30 mL and each was lysed by probe sonication (Misonix S-4000 Sonicator Ultrasonic Processor equipped with a Dual Horn probe) with 20% amplitude and an on/off pulse of 5 s for a total sonication time of 10 min. The cell lysates were centrifuged at 48,384 g (Beckman coulter centrifuge Avanti J-26 with rotor JA-25.50) for 15 min at 4° C., the soluble fraction was collected and mixed with 2 mL of Ni-NTA resin at 4° C. for 15 min. The resin was washed with 10×10 mL of wash buffer (50 mM Tris pH 7.5, 500 mM NaCl, 30 mM imidazole) and eluted with elution buffer (50 mM Tris pH 7.5, 500 mM NaCl, 250 mM imidazole) until the Bradford assay, which detects protein, indicated all protein had eluted. The protein solution was dialyzed (MWCO 8 kDa) at 4° C. against 4 L of 50 mM phosphate buffer pH 7.0 with 100 mM NaCl and 2 mM DTT for 4 hours, then transferred to 4 L of 50 mM phosphate buffer pH 7.0 with 100 mM NaCl and dialyzed another 24 h, changing the buffer 2 more times. 12 mg of SH3-rhFGF2 was collected. The protein was sterile-filtered (0.22 µM) and verified by ESI mass spectrometry (ABI/Sciex Qstar mass spectrometer) and denaturing gel electrophoresis (FIGS. 5 and 6). An extinction coefficient of 38390 $M^{-1} cm^{-1}$ and MW of 27.7 kDa, respectively, were used to identify SH3-rhFGF2.

Bioactivity Assay for SH3-rhFGF2

The bioactivity of SH3-rhFGF2 was determined in vitro using mice neural stem cell cultures as previously described[32] with 10 ng/mL rhFGF2 and 10 ng/mL (rhFGF2 equivalent) of SH3-rhFGF2 (FIG. 7).

Preparation of HAMC and HAMC-Peptide Hydrogels

Physical hydrogel blends of hyaluronan (HA) and methyl cellulose (MC) or methylcellulose-SH3-binding peptide (MC-peptide) were prepared in the following compositions with aCSF or SH3-rhFGF2: 1 wt % 2600 kg/mol HA, 3 wt % 300 kG/mol MC or MC-peptide (1:3 HAMC or HAMC-peptide). For example, to prepare 1000 µl of 1:3 HAMC or HAMC-peptide, 10 mg HA and 30 mg MC or MC-peptide was mechanically dispersed in 960 µL cold aCSF (HAMC) or 480 µL cold aCSF and 480 µL cold 40 µM SH3-rhFGF2 solution with 0.4 mg/mL heparin using a planetary mixer (Flacktek Inc., Landrum, USA) and chilled for 1 h. At this time the gels were dispersed again using a planetary mixer and then centrifuged at 16,162 g (Sigma 1-14 microcentrifuge) for 1 min at 4° C. to remove air bubbles. The solutions were left to dissolve overnight at 4° C. before use.

In Vitro Release of SH3-rhFGF2 from HAMC and HAMC-Peptide

HAMC and HAMC-peptide hydrogels were prepared as described above with SH3-rhFGF2 (20 µM) vs. controls without protein to ensure the hydrogel itself did not interfere with the ELISA detection of SH3-rhFGF2. Each hydrogel was loaded into a 250 µL Hamilton syringe (Hamilton Company USA, Reno, USA) equipped with a 30 G needle and injected into the bottom of a 2.0 mL microcentrifuge tube. The gel was allowed to settle for 1 h at 4° C. and then pre-warmed to 37° C. for 5 min to induce gel formation. 900 µL of pre-warmed aCSF with 0.2 mg/mL heparin (release buffer) was added to each tube, approximating the dilution of hydrogel to CSF of 1:10 v/v that is expected in vivo when injected into the intrathecal space of a rat. Samples were incubated at 37° C. on an orbital shaker and release buffer was fully removed and replaced with fresh release buffer at t=1, 2, 4, 8, 16, 24, 48, 72, 120, 168 and 240 h. Aliquots were frozen at −20° C. until assayed for SH3-rhFGF2 detection. A sandwich ELISA (Peprotech, Human FGF-basic ELISA Development Kit) was used to determine the concentration of SH3-rhFGF2 in the aCSF removed at each timepoint (n=4).

Normalization of In Vitro Release Data

In vitro release profiles have been normalized to total amount of protein detected (by ELISA) (FIG. 8). After release, gels were disrupted and assayed for remaining protein content. Total protein detected from each group was highly different: HAMC (73.6±1.9) %, HAMC-weak binder (44.2±9.3) % and HAMC-strong binder (10.1±1.1) %. Importantly, the amount of protein detected is related to the rate of protein release. That is, the faster the rate of protein release, the more total protein was detected. Nakamura et al. have shown that incubation of FGF-2 for less than 1 day at 37° C. reduces bioactivity to <10%.[52] Since sampling during the first day of release is frequent, protein instability at 37° C. does not contribute greatly. However, after 1 day, the sampling interval decreases to 1 day or more, in which case loss of detectability due to incubation of the protein at 37° C. has a significant effect.

Chondroitinase ABC-SH3 Fusion Expression and Purification

To obtain His-SH3-ChABC-FLAG DNA, a sequence coding for ChABC with a C-terminal FLAG tag was subcloned into a pET28b+ vector already containing the sequence coding for His-SH3 followed by a flexible linker region as described above. ChABC-FLAG was inserted into this target vector using the restriction enzymes XhoI and EagI. The plasmid was transformed into chemically competent BL21(DE3) *E. coli* cells, plated on Leuria-Bertani (LB)-agar plates containing 50 μg/mL kanamycin and incubated overnight at 37° C. Resulting clones were grown in starter cultures of 20 mL of Leuria-Bertani (LB) broth containing 50 μg/mL kanamycin overnight at 37° C. Starter cultures were inoculated into 1.8 L of Terrific Broth (TB) supplemented with 0.8% glycerol, 50 μg/mL kanamycin, and 5 drops of Anti-foam 204. Cells were grown with air sparging at 37° C. until an $OD_{600}$ of 0.6-0.8 was reached. Cells were then induced with a final concentration of 0.8 mM IPTG and grown overnight at 22° C. Cells were collected by centrifugation for 15 min at 6000 rpm and 4° C. (Beckman coulter centrifuge Avanti J-26 with rotor JLA-8.1000), resuspended in 60 mL of buffer (50 mM Tris pH 7.5, 500 mM NaCl, 5 mM imidazole) and sonicated for 10 min at 30% amplitude with a pulse of 2 s (Misonix S-4000 Sonicator Ultrasonic Processor equipped with a Dual Horn probe). The slurry was centrifuged at 45,000 G for 15 min at 4° C. (Beckman coulter centrifuge Avanti J-26 with rotor JA-25.50). The liquid fraction was incubated with 2 mL of Ni-NTA resin solution for 15 min at 4° C. The resin was collected in a column with a glass frit and washed 10×10 mL with wash buffer (50 mM Tris, pH 7.5, 500 mM NaCl, 30 mM imidazole) and eluted with elution buffer (50 mM Tris, pH 7.5, 500 mM NaCl, 250 mM imidazole). Eluate was concentrated to ~1 mL using a Vivaspin 10,000 kDa cutoff centrifugal filter (Sartorius) and further purified by size-exclusion chromatography (SEC) in 10 mM phosphate buffer (pH 8.0, 50 mM sodium acetate) using fast protein liquid chromatography (FPLC, Hi-load 16/60 Superdex 200 prep grade column, AKTA Explorer 10, Amersham Pharmacia). Protein concentrations were determined by absorbance at 280 nm using an ND-1000 Nanodrop spectrophotometer.

Chondroitinase ABC Kinetic Activity Assay

Kinetic ChABC activity assay tracks the absorbance at 232 nm of the double bond formed after ChABC digestion of chondroitin sulfate A (CS-A). 10 μl of recombinant ChABC-SH3 (1 μg) was placed into a Costar 96-well UV transparent plate (Corning Inc., Corning, USA). 90 μl of 10 mg/mL chondroitin sulphate A (CS-A) was then placed simultaneously into each well using a multi-pipette. The plate was immediately placed inside a TECAN Infinite M200 Pro spectrophotometer and measured every 20 s at 232 nm for 20 min at room temperature with 5 s of orbital shaking between each measurement. 100 μl of CS-A with no ChABC was used as a blank measurement and was subtracted from the measured absorbance at each time point.

Dimethylmethylene Blue Activity Assay

The DMMB assay for sulfated glycosaminoglycans was performed as previously described[53,54]. 10 μl of 0.5 mg/mL decorin from bovine articular cartilage was incubated in a 96-well plate with 10 μl of ChABC-SH3 solution (released or positive control) at 37° C. with gentle shaking for 24 h. The plate was covered and water was placed in all unused wells to prevent evaporation of reagents. 180 μl of 1,9-dimethylmethylene blue working solution (16 mg of dye in 1 L of water containing 3.04 g glycine, 2.37 g NaCl and 95 mL, 0.1 M HCl) was added and to all wells and the plate was immediately read at 530 nm in a TECAN Infinite M200 Pro spectrophotometer. Decorin incubated with no ChABC-SH3 was used as a blank.

Double-Tag ELISA for ChABC-SH3

200 μl of ChABC-SH3 protein sample or known standard was added to each well of a Hisorb Ni-NTA 96-well plate (Qiagen, Toronto, ON) and incubated for 2 h at 37° C. on an orbital shaker. The wells were then washed with 250 μl 1×PBS three times for 10 s each with vigorous tapping and blotted dry on paper towels. 200 μl of anti-FLAG antibody coupled with HRP diluted 1:5000 in 1×PBS was added to each well and incubated at 37° C. for 2 h on an orbital shaker. The wells were then washed as above and blotted dry. 100 μl of 2,2'-azino-bis(3-ethylbenzothiazoline-6-sulphonic acid) (ABTS) was then added to each well and incubated at room temperature for 25 min on an orbital shaker. The absorbance was measured at 405 nm with a wavelength correction at 650 nm. Protein concentration was calculated based on the linear range of a standard curve from the same plate. Protein samples were diluted to fit within this linear range.

Hydrogel Preparation

MC-peptide was synthesized as described above. 20 mg total of MC and MC-peptide were dissolved in artificial cerebrospinal fluid (aCSF: 350 mM NaCl, 3 mM KCl, 0.8 mM $MgCl_2$, 1.4 mM $CaCl_2$, 1.5 mM $Na_2HPO_4$, 0.2 mM $NaH_2PO_4$, pH 7.6). The relative amounts of modified and unmodified MC used depended on the desired peptide to protein ratio. The volume of aCSF used depended on the concentration of the ChABC-SH3 solution. For example, with a ChABC-SH3 stock solution at 5.56 mg/mL and MC-peptide at 216.3 μmol peptide/g MC the following amounts were used to make 400 μl of 5% w/v gel with a peptide:protein ratio of 100:1, 43 μl of ChABC solution (0.00182 μmol), 0.844 mg of MC-peptide (0.182 μmol), 19.16 mg unmodified MC, 400 μl aCSF. The MC solution was mixed using a SpeedMixer DAC 150 FV2 (FlackTek Inc., Landrum, USA) for 4 min at 35,000 rpm and centrifuged at 14,000 rpm in a microcentrifuge for 10 min at 4° C. 60 μg of ChABC was then added to bring the total volume of gel to 400 μl (5% MC/MC-peptide). The protein was incorporated into the gel by speedmixing for 1 min followed by centrifugation at 10,000 rpm for 4 min. The resulting hydrogel was allowed to equilibrate overnight before being used.

Release Studies

100 μl of the MC-peptide containing ChABC-SH3 was injected into each of three 2 mL tubes. The tubes were gently centrifuged to allow the gel to spread across the whole tube bottom. The tubes were then placed at 37° C. for 10 min to allow the gels to set. 400 μl of aCSF was then carefully placed on top of the gel. The gels were kept in a 37° C. incubator with gentle shaking. At designated timepoints (0, 1, 2, 5, 7 d) the supernatant was completely removed and replaced with fresh aCSF. MC-peptide gel without ChABC-SH3 was monitored in a similar manner and used as a blank for each timepoint. Release samples were stored at −80° C. until ready for analysis by ELISA.

Advantageously, a pair of binding moieties is selected to reversibly bind specifically with each other. In the context of this invention, "specific" means that the polymer-bound moiety binds preferentially to its counterpart linked to the biologically active portion of the chimeric molecule. While there may be non-specific interactions between the polymer and the chimeric molecule, the release is controlled predominantly by the affinity (or dissociation constant, $K_d$) between the binding partners covalently linked to the polymer and chimeric molecule, respectively.

By "extended release" is meant that the interaction of the binding moieties that are part of the composition results in release that is slower from the same composition that does not have such binding moieties. The amount of release, for comparison purposes, is based on the amount of active agent released from the composition in comparison to that initially present in the composition. In various embodiments, it takes at least 24 hours for at least 80% of the agent to be released, or at least 2 days for at least 80% of the agent to be released, or at least 3 days for at least 80% of the agent to be released, or at least 4 days for 80% of the agent to be released, or at least 5 days of the agent to be released, or at least 6 days for 80% of the agent to be released, or at least 7 days for at least 80% of the agent to be released, or at least 8 days for at least 80% of the agent to be released, or at least 9 days for at least 80% of the agent to be released, or at least 10 days for at least 80% of the agent to be released, or at least 11 days for at least 80% of the agent to be released.

The value of $K_d$ is evaluated by [is the a particular method?], and is the $K_d$ as determined for binding moieties or partners as they bind with each other when not part of the composition. $K_d$ values of the invention are in units of molar (M) unless specified otherwise.

$K_d$ is selected, for example, such that the composition provides extended release of the active agent, and can be used, for example, in combination with the ratio of polymer-bound binding moiety to the amount of drug-bound moiety to obtain a desired level extended release. Preferably, a $K_d$ is in the range of $10^{-3}$ to $10^{-9}$, but may be in the range of $10^{-3}$ to $10^{-7}$, $10^{-4}$ to $10^{-7}$, or in the range of $10^{-3}$ to $10^{-6}$, or in the range of $10^{-4}$ to $10^{-6}$, or in the range of $10^{-5}$ to $10^{-7}$, in the range of $10^{-3}$ to $10^{-5}$, or about $10^{-3}$ or about $10^{-4}$, or about $10^{-5}$ or about $10^{-6}$, or about $10^{-7}$.

A database of protein domains and their corresponding binding proteins is available at http://www.cellsignal.com/reference/domain/index.html. Lists of binding domains are available at: http://pawsonlab.mshri.on.ca/index.php?option=com_content&task=section&id=3<e mid=64.

In connection with the ChABC embodiment, a change in the ratio of a matrix-bound binding partner to the agent-bound binding partner from 100:1 to 300:1 slows release of an active agent from the composition. Preferably, the ratio in an extended release composition is at least 10:1, and can be between 10:1 and 700:1, or between 10:1 and 600:1, or between 10:1 and 500:1, or between 10:1 and 400:1, or between 20:1 and 700:1, or between 30:1 and 700:1, or between 40:1 and 700:1, or between 50:1 and 700:1, or between 50:1 and 700:1, or between 50:1 and 600:1, or between 50:1 and 500:1, or between 50:1 and 400:1, or between 50:1 and 350:1, or between 80:1 and 700:1, or between 80:1 and 600:1, or between 80:1 and 500:1, or between 80:1 and 400:1, or between 80:1 and 400:1, or is about 80:1, or about 90:1, or about 1000:1, or about 110:1, or about 120:1, or about 130:1, or about 140:1, or about 150:1, or about 170:1, or about 190:1, or about 200:1, or about 210:1, or about 220:1, or about 230:1, or about 240:1, or about 250:1, or about 260:1, or about 270:1, or about 280:1, or about 290:1, or about 300:1, or about 310:1, or about 320:1, or about 330:1, or about 340:1, or about 350:1, or about 360:1, or about 370:1, or about 380:1, or about 390:1, or about 400:1, or about 410:1, or about 420:1, or about 430:1, or about 440:1, or about 450:1, or about 460:1, or about 470:1, or about 480:1, or about 490:1, or about 500:1, or about 510:1, or about 520:1, or about 530:1, or about 540:1, or about 550:1, or about 560:1, or about 570:1, or about 580:1, or about 590:1, or about 600:1, or about 610:1, or about 620:1, or about 630:1, or about 640:1, or about 650:1, or about 660:1, or about 670:1, or about 680:1, or about 690:1, or about 700:1, or between about any combination of the foregoing listed ratios.

An overall load of the polymer-bound binding moiety can be achieved by inclusion in the composition of an additional unmodified polymer i.e., a polymer that does not have the binding moiety bound thereto.

As discussed in connection with specific embodiments, a particular polymer incorporated in the composition was methyl cellulose (MC). A portion of the hydroxyl groups of this starting material are thus methylated and unavailable for covalent linkage with a binding moiety. The degree of substitution of the particular material used was 1.7/3. The presence of the methylated groups limits the number of hydroxyl in a monomeric unit (glucose in the case of methyl cellulose) that can become covalently bound to a binding moiety in the product composition. Such a monomeric unit containing 1 methoxy group thus has at most two hydroxyl groups that can be linked to a binding moiety, a monomeric unit containing 2 methoxy groups has one free hydroxyl group. In various aspects, each monomeric unit present the polymer from which the polymer of the composition is produced can include, on average, between 0.25 and 3 functional groups capable of forming a covalent linkage with the second binding moiety from which the polymer of the composition is produced. This number can be between 0.25 and 2.5, 0.25 and 2.4, 0.25 and 2.3, 0.25 and 2.2, 0.25 and 2.1, 0.25 and 2.0, 0.25 and 1.9, 0.25 and 1.8, 0.5 and 2.5, 0.5 and 2.0, or about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5, or any range between any of the fore-listed.

As mentioned elsewhere, the substitution rate of SH3-binding peptide per monomeric (glucose) units was about 1:15 in the SH3-rhFG2 example. This ratio can be, for example, between 1:100 and 1:1, or between 1:100 and 1:5, or between 1:100 and 1:20, or can be about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:25, about 1:30, about 1:35, about 1:40, about 1:45, about 1:50, about 1:55, about 1:60, about 1:65, about 1:70, about 1:75, about 1:80, about 1:85, about 1:90, about 1:95, about 1:100, or can be any range or ratios between any of the fore-listed ratios.

The inventors have disclosed components and parameters to be used to prepare compositions of the invention as well as the compositions themselves to be used within the embodiments described herein. It is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular composition is disclosed and a number of modifications that can be made to a number of molecules including the compounds are discussed, specifically contemplated is each and every combination and permutation of the compound and the modifications that are possible unless specifically indicated to the contrary. Thus, if a class of molecules, or composition elements L, M and N are disclosed as well as a class of molecules or elements R, S and T and an example of a combination molecule, M-S is disclosed, then even if each is not individually recited each is individually and collectively contemplated meaning combinations, L-R, L-S, L-T, M-R, M-T, N-R, N-S and N-T are considered disclosed.

A "hydrogel" is made up of a three-dimensional hydrophilic organic polymeric network, which can be natural or synthetic, that entraps molecules of preferably water, or other solution to form a gel. Hydrogels for therapeutics are biocompatible, and are preferably designed such that they will form in situ and these are termed injectable hydrogels. An "injectable hydrogel" or injectable hydrogel polymer refers to a solution which is capable of forming a hydrogel once it has been injected into a mammal.

A biocompatible hydrogel is not toxic to the biologically active agent of a therapeutic composition contained in the hydrogel and a biocompatible material generally behaves in the body as intended.

The phrase "reverse thermal gelation" describes an increase in viscosity of a substance upon an increase in temperature. An example is a substance that is a liquid and having low viscosity at room temperature which increases in viscosity upon an increase in temperature e.g. to human body temperature of about 37° C. The increase in viscosity leads to conversion of the substance to a more rigid semi-solid state, here a gel. The increase in temperature which effects gelation may be between any two temperatures, for example 0° C. and 55° C., but in the case of medicaments for human use, gelation is effected at a temperature within the range of 0° C. to 37° C. In certain embodiments where it is desirable to inject a pharmaceutical composition at room temperature e.g., around 20° C., it can be preferred that the composition undergo gelation above this temperature.

Here, a polymeric moiety exhibits reverse thermal gelation when an aqueous solution of a polymer which corresponds to the polymeric moiety, for example a polymer not covalently to a peptidyl ligand exhibits reverse thermal gelation.

A variety of polymers exhibit reverse thermal gelation. Each polymer may be characterized by a critical gelation temperature, wherein gelation is effected at the critical gelation temperature or at temperatures above the critical gelation temperature.

"Critical gelation temperature" refers to the lowest temperature at which some gelation of a material is observed, for example, by an increase in shear storage modulus.

The polymeric moiety may be selected so as to impart to the conjugate e.g., MC-peptide containing the same reverse thermal gelation that is characterized by a critical gelation temperature within a temperature range, for example 0° C. to 55° C. which allows for convenient manipulation of the properties of the polymer having e.g., a peptidyl ligand covalently linked thereto (conjugate) by exposure to ambient temperature above and/or below the critical gelation temperature.

As mentioned above, the critical gelation temperature of the polymer may be selected, for example, based on the intended use or desired properties of a conjugate. For example, the critical gelation temperature can be selected so that the conjugate is in a gelled state at a physiological temperature (about 37° C. for human use) but not at room temperature, such that gelation may be effected in vivo. In another example, the critical gelation temperature may be selected such that the conjugate is in a gelled state at room temperature but not at a moderately lower temperature, such that gelation may be effected, for example, by removal from refrigeration.

Optionally, the reverse thermal gelation of the conjugate occurs at a temperature below 55° C., optionally below 50° C., optionally below 40° C., and optionally below 30° C. Optionally, the reverse thermal gelation occurs at a temperature below about 37° C., such that at a physiological temperature of about 37° C., the conjugate is in a gelled state.

Optionally, the reverse thermal gelation of the conjugate occurs at a temperature above 0° C., optionally above 10° C., optionally above 20° C. and optionally above 30° C.

In some embodiments, the reverse thermal gelation of the conjugate occurs upon an increase of temperature from 0° C. to 55° C., optionally from 10° C. to 55° C., optionally from 10° C. to 40° C., optionally from 15° C. to 37° C., and optionally from 20° C. to 37° C. Reverse thermal gelation which occurs upon an increase of temperature from a room temperature (e.g., about 20° C., about 25° C.) to a physiological temperature (e.g., about 37° C.) are particularly useful for some applications, particularly medical applications, as gelation can be induced by transferring the conjugate from a room temperature environment to a physiological temperature, for example, by placing the conjugate in a body.

"Shear modulus" is the ratio of shear stress to the shear strain. The shear modulus may be a complex variable, in which case the "storage modulus" is the real component and the "loss modulus" is the imaginary component. The storage modulus and loss modulus in viscoelastic solids measure the stored energy, representing the elastic portion, and the energy dissipated as heat, representing the viscous portion.

In some embodiments, the reverse thermal gelation described herein increases a shear storage modulus (also referred to herein as "storage modulus", or as "G'") of the aqueous solution of the conjugate by at least ten-fold, optionally at least 30-fold, optionally at least 100-fold, and optionally at least 300-fold.

In some embodiments, the reverse thermal gelation described herein increases a shear storage modulus of the aqueous solution to at least 5 Pa, optionally at least 15 Pa, optionally at least 20 Pa, optionally at least 50 Pa, optionally at least 100 Pa, and optionally at least 200 Pa In some embodiments, the shear storage modulus of the aqueous solution containing the conjugate before reverse thermal gelation (e.g., at a temperature below a temperature at which gelation occurs) is less than 2 Pa, optionally less than 1 Pa, optionally less than 0.5 Pa, and optionally less than 0.2 Pa.

Optionally the hydrogel is characterized by a shear storage modulus of at least 15 Pa (optionally at least 50 Pa, optionally at least 100 Pa, and optionally at least 200 Pa) at 37° C.

The disclosures of all documents referred to herein by reference, as are the contents of websites referred to herein, as though fully reproduced herein in their entirety.

REFERENCES (1) Bradbury, E. J.; Moon, L. D. F.; Popat, R. J.; King, V. R.; Bennett, G. S.; Patel, P. N.; Fawcett, J. W.; McMahon, S. B. *Nature* 2002, 416, 636-640.
(2) Schnell, L.; Schneider, R.; Kolbeck, R.; Barde, Y.-A.; Schwab, M. E. *Nature* 1994, 367, 170-173.
(3) Moon, L. D. F.; Asher, R. A.; Rhodes, K. E.; Fawcett, J. W. *Nature Neuroscience* 2001, 4, 465-466.
(4) Putney, S. D.; Burke, P. A. *Nat Biotech* 1998, 16, 153-157.
(5) LaVan, D. A.; McGuire, T.; Langer, R. *Nat Biotech* 2003, 21, 1184-1191.
(6) Wang, N. X.; von Recum, H. A. *Macromolecular Bioscience* 2011, 11, 321-332.
(7) Perez, C.; Castellanos, I. J.; Costantino, H. R.; Al-Azzam, W.; Griebenow, K. *Journal of Pharmacy and Pharmacology* 2002, 54, 301-313.
(8) Kumar, V.; Prud'homme, R. K. *Journal of Pharmaceutical Sciences* 2008, 97, 4904-4914.
(9) Ho, Y.-C.; Mi, F.-L.; Sung, H.-W.; Kuo, P.-L. *International Journal of Pharmaceutics* 2009, 376, 69-75.
(10) Lee, J. S.; Go, D. H.; Bae, J. W.; Lee, S. J.; Park, K. D. *Journal of Controlled Release* 2007, 117, 204-209.
(11) Tae, G.; Scatena, M.; Stayton, P. S.; Hoffman, A. S. *Journal of Biomaterials Science-Polymer Edition* 2006, 17, 187-197.
(12) Yoon, J. J.; Chung, H. J.; Lee, H. J.; Park, T. G. *Journal of Biomedical Materials Research Part A* 2006, 79A, 934-942.
(13) Maxwell, D. J.; Hicks, B. C.; Parsons, S.; Sakiyama-Elbert, S. E. *Acta Biomaterialia* 2005, 1, 101-113.
(14) Sakiyama-Elbert, S. E.; Hubbell, J. A. *Journal of Controlled Release* 2000, 69, 149-158.
(15) Sakiyama-Elbert, S. E.; Hubbell, J. A. *Journal of Controlled Release* 2000, 65, 389-402.
(16) Wood, M. D.; Borschel, G. H.; Sakiyama-Elbert, S. E. *Journal of Biomedical Materials Research Part A* 2009, 89A, 909-918.
(17) Wood, M. D.; Sakiyama-Elbert, S. E. *Journal of Biomedical Materials Research Part A* 2008, 84A, 300-312.
(18) Nie, T.; Baldwin, A.; Yamaguchi, N.; Kiick, K. L. *Journal of Controlled Release* 2007, 122, 287-296.
(19) Lin, C.-C.; Anseth, K. S. *Advanced Functional Materials* 2009, 19, 2325-2331.
(20) Fan, J. A.; Xiao, Z. F.; Zhang, H. T.; Chen, B.; Tang, G. Q.; Hou, X. L.; Ding, W. Y.; Wang, B.; Zhang, P.; Dai, J. W.; Xu, R. X. *Journal of Neurotrauma* 2010, 27, 1671-1683.
(21) Gupta, D.; Tator, C. H.; Shoichet, M. S. *Biomaterials* 2006, 27, 2370-2379.
(22) Cooke, M. J.; Wang, Y.; Morshead, C. M.; Shoichet, M. S. *Biomaterials* 2011, 32, 5688-5697.
(23) Baumann, M. D.; Kang, C. E.; Stanwick, J. C.; Wang, Y.; Kim, H.; Lapitsky, Y.; Shoichet, M. S. *Journal of Controlled Release* 2009, 138, 205-213.
(24) Kang, C. E.; Tator, C. H.; Shoichet, M. S. *Journal of Controlled Release* 2010, 144, 25-31.
(25) Thuret, S.; Moon, L. D. F.; Gage, F. H. *Nat Rev Neurosci* 2006, 7, 628-643.
(26) Ramer, M. S.; Priestley, J. V.; McMahon, S. B. *Nature* 2000, 403, 312-316.
(27) Rabchevsky, A. G.; Fugaccia, I.; Turner, A. F.; Blades, D. A.; Mattson, M. P.; Scheff, S. W. *Experimental Neurology* 2000, 164, 280-291.
(28) Brunswick, M.; Finkelman, F.; Highet, P.; Inman, J.; Dintzis, H.; Mond, J. *The Journal of Immunology* 1988, 140, 3364-3372.
(29) Shu, X. Z.; Liu, Y.; Luo, Y.; Roberts, M. C.; Prestwich, G. D. *Biomacromolecules* 2002, 3, 1304-1311.
(30) Stollar, E. J.; Garcia, B.; Chong, P. A.; Rath, A.; Lin, H.; Forman-Kay, J. D.; Davidson, A. R. *Journal of Biological Chemistry* 2009, 284, 26918-26927.
(31) Deyev, S. M.; Waibel, R.; Lebedenko, E. N.; Schubiger, A. P.; Pluckthun, A. *Nat Biotech* 2003, 21, 1486-1492.
(32) Wylie, R. G.; Shoichet, M. S. *Biomacromolecules* 2011, 12, 3789-3796.
(33) Ritger, P. L.; Peppas, N. A. *Journal of Controlled Release* 1987, 5, 23-36.
(34) Huang, X.; Brazel, C. S. *Journal of Controlled Release* 2001, 73, 121-136.
(35) Kang, C. E.; Poon, P. C.; Tator, C. H.; Shoichet, M. S. *Tissue Engineering Part A* 2009, 15, 595-604.
(35) Kang, C. E., Poon, P. C., Tator, C. H. & Shoichet, M. S., *Tissue Engineering Part A* 15, 595-604 (2008).
(36) Suzuki, T. et al., *Cell Transplantation* 16, 493-503 (2007).
(37) Ma, J. et al., *Molecular Vision* 17, 1759-1770 (2011).
(38) Soleman, S., Yip, P. K., Duricki, D. A. & Moon, L. D. F., *Brain* 135, 1210-1223 (2012).
(39) Hill, J. J. et al., *Proceedings of the National Academy of Sciences* 109, 9155-9160 (2012).
(40) Dmitrieva, N. et al., *Clinical Cancer Research* 17, 1362-1372 (2011).
(41) Tester, N. J., Plaas, A. H. & Howland, D. R., *Journal of Neuroscience Research* 85, 1110-1118 (2007).
(42) Lee, H., McKeon, R. J. & Bellamkonda, R. V., *Proceedings of the National Academy of Sciences* 107, 3340-3345 (2010).
(43) Kwon, B. K. et al., *Journal of Neurotrauma* 28, 1589-1610 (2011).
(44) Hyatt, A. J. T. et al., *Journal of Controlled Release* 147, 24-29 (2010).
(45) Rossi, F. et al., *Journal of Functional Biomaterials* 3, 199-208 (2012).
(47) Smith, P. K. et al., *Analytical Biochemistry* 150, 76-85 (1985).
(46) Huang, Y.-C. et al., *Carbohydr Polym* 84, 788-793 (2011).
(49) Appel, E. A. et al., *Biomaterials* 33, 4646-4652 (2012).
(50) Stempfer, G., Holl-Neugebauer, B., Kopetzki, E. & Rudolph, R., *Nat Biotechnol* 14, 481-484 (1996).
(51) Wang, W., *International Journal of Pharmaceutics* 185, 129-188 (1999).
(52) Nakamura, S.; Kanatani, Y.; Kishimoto, S.; Nakamura, S.-i.; Ohno, C.; Horio, T.; Masanori, F.; Hattori, H.; Tanaka, Y.; Kiyosawa, T.; Maehara, T.; Ishihara, M. *Journal of Biomedical Materials Research Part A* 2009, 91A, 814-823.
(53) Mort, J. S. & Roughley, P. J. in *Methods in Molecular Medicine* Vol. 135 *Methods in Molecular Medicine* (ed A. P. Cope) 201-209 (2007).
(54) Liu, T., Xu, J., Chan, B. P. & Chew, S. Y., *Journal of Biomedical Materials Research Part A* 100A, 236-242 (2012).

The invention claimed is:

1. An extended release composition comprising:
   (a) a chimeric molecule comprising a biologically active molecule, and a first binding moiety covalently linked thereto; and
   (b) a polymer comprising a polymeric matrix having a second binding moiety, which specifically binds with the first binding moiety, covalently linked to the matrix, wherein the first and second binding moieties are reversibly bound to each other in a complex having a dissociation constant Kd of between $10^{-3}$ and $10^{-9}$ M.

2. The composition of claim 1, wherein the polymeric matrix comprises monomeric units, wherein, on average, each unit from which the matrix is produced includes between 0.25 and 3 functional groups capable of forming a covalent linkage with the second binding moiety from which the polymer is produced, and, on average, the fraction of said monomeric units of the polymeric matrix which form said covalent linkage with at least one said second binding moiety is between 1/50 and 1/1, inclusively.

3. The composition of claim 2, wherein, on average, the polymer includes 1 second binding moiety covalently linked to at least 1 of 100 monomeric units and up to 1 of 1 monomeric units.

4. The composition of claim 3, wherein each said monomeric unit covalently linked to a second binding moiety has from 1 to 3 said second binding moieties covalently linked thereto.

5. The composition of claim 3, wherein the polymeric matrix comprises a cellulose derivative.

6. The composition of claim 3, wherein the polymeric matrix comprises a hydroxyl-substituted polysaccharide having a degree of substitution (DS) of between $0.5 \leq DS \leq (N-0.2)$, wherein N is the total theoretical degree of substitution for a monomeric unit of the polymeric matrix, wherein said substituent is an alkyl group.

7. The composition of claim 1, wherein the polymer is selected from the group consisting of polyacrylates; ethylene-vinyl acetates; acyl substituted cellulose acetates; non-degradable polyurethanes; polystyrenes; polyvinyl chlorides; polyvinyl fluorides; poly(vinyl imidazoles); chlorosulphonate polyolefins; polyethylene oxides; poly(propylene oxides); poly(ethylene), poly(propylene); cellulose or derivatives thereof; polyesters, poly(alpha hydroxyl esters), poly(lactide), poly(glycolide), copolymers of lactide and glycolide, polyhydroxybutyrate, polycaprolactone, copolymers of lactic acid and lactone, copolymers of lactic acid and poly(ethylene glycol), copolymers of α-hydroxy acids and α-amino acids (polydepsipeptides), poly(peptides), polyanhydrides, polyorthoesters, polyphosphazenes, copolymers of hydroxybutyrate and hydroxyvalerate, poly(ethylene carbonate), polyethyleneterephthalate or mixtures of these polymers, lactide homopolymers poly(L lactide), poly(D,L-lactide), copolymers of lactide and glycolide, 50:50 poly(DL lactide co glycolide) (PLG), polycarbonates, degradable polyurethanes, poly(ortho esters), poly(dioxanone), hyaluronan or derivatives thereof, methyl cellulose or derivatives thereof, alginate, chitosan, agarose, oligomers of poly(lactic acid), lactides, copolymers of PEG and amino acids, conjugates of PEG with polysaccharides, and a conjugate produced from dextran and polyoxyethylene glycol monomethyl ether.

8. The composition of claim 1, wherein the biologically active molecule is selected from the group consisting of acetaminophen, baclofen, ibuprofen, fluriprofen, ketoprofen, voltaren, phenacetin, salicylamide, naproxen, indomethacin, chlorpheniramine maleate, phenindamine tartrate, pyrilamine maleate, doxylamine succinate, phenyltoloxamine citrate, diphenhydramine hydrochloride, promethazine, brompheniramine maleate, dexbrompheniramine maleate, clemastine fumarate, triprolidine, dextromethorphan hydrobromide, guaifenesin, phenylephrine hydrochloride, phenylpropanolamine hydrochloride, pseudoephedrine hydrochloride, ephedrine, amebicides, broad and medium spectrum fungal medications, monobactams and viral agents, theophylline, albuterol, terbutaline, diltiazem, propranolol, nifedepine, clonidine, alpha adrenoceptor agonists, alpha receptor blocking agents, alpha and beta receptor blocking agents, angiotensin converting enzyme inhibitors, beta blocking agents, calcium channel blockers, cardiac glycosides, thioridazine, diazepam, meclizine, ergoloid mesylates, chlorpromazine, carbidopa, levodopa, potassium chloride, lithium carbonate, iron, chromium, molybdenum, potassium, minocycline, cyclosporine A, synthetic thyroid hormone, thyroxine sodium, human chorionic gonadotrophin (HCG), corticotrophin, human growth hormone (HGH), erythropoietin (EPO), ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, GM1 ganglioside, cAMP, water-soluble vitamins, veterinary formulations, EGF, FGF2, chondroitinase ABC (ChABC), neurotrophins, peptides, peptide mimetics DNA, and, small interfering RNAs.

9. A composition according to claim 1, wherein the polymer matrix is a reverse thermal gelling polymer hydrogel.

10. A composition according to claim 1, wherein the polymer matrix comprises methylcellulose.

11. A composition according to claim 10, further comprising hyaluronan.

12. A composition according to claim 11, further comprising unmodified methylcellulose.

13. A composition according to claim 12, wherein the first binding moiety of the chimeric molecule comprises an SH3 binding domain, and the second binding moiety comprises a peptidyl ligand.

14. A composition according to claim 13, wherein said peptidyl ligand is selected from the group consisting of KPPVVKKPHYLS (SEQ ID NO:6) and KKTKPTPPPKPSHLKPK (SEQ ID NO:7), and a combination thereof.

15. A composition according to claim 14, wherein the biologically active molecule comprises fibroblast growth factor (FGF2).

16. A composition according to claim 14, wherein the biologically active molecule comprises chondroitinase ABC (ChABC).

17. A composition according to claim 5, wherein the polymer matrix is a reverse thermal gelling polymer hydrogel.

18. An extended release composition comprising:
(a) a chimeric molecule comprising a biologically active molecule, and a first binding moiety covalently linked thereto; and
(b) a polymer comprising a polymeric matrix having a second binding moiety, which specifically binds with the first binding moiety, covalently linked to the matrix, wherein the first and second binding moieties are reversibly bound to each other and the ratio of the second binding moiety to the first binding moiety in the composition is at least 10:1.

19. An injectable pharmaceutical composition comprising:
(a) a chimeric protein comprising a biologically active peptide and a protein binding domain fused thereto; and
(b) a biocompatible injectable hydrogel polymer comprising a polymeric matrix having a peptidyl ligand covalently linked thereto, wherein the peptidyl ligand is reversibly bound to the protein binding domain of the chimeric protein to form a complex having a dissociation constant Kd of between $10^{-3}$ and $10^{-9}$ M and provide extended delivery of the protein to a subject for at least one week.

20. A composition according to claim 19, wherein the protein binding domain is an SH3 domain.

* * * * *